(12) United States Patent
Alas et al.

(10) Patent No.: US 12,245,805 B2
(45) Date of Patent: Mar. 11, 2025

(54) COMPOSITIONS, SYSTEMS, KITS, AND METHODS FOR NEURAL ABLATION

(71) Applicant: Avent, Inc., Alpharetta, GA (US)

(72) Inventors: Guillermo Alas, Alpharetta, GA (US); Michael G. Smith, Alpharetta, GA (US); Sherry E. Adesina, Tucker, GA (US); Alencia V. Washington, Roswell, GA (US)

(73) Assignee: Avent, Inc., Alpharetta, GA (US)

( * ) Notice: Subject to any disclaimer, the term of this patent is extended or adjusted under 35 U.S.C. 154(b) by 609 days.

(21) Appl. No.: 17/011,927

(22) Filed: Sep. 3, 2020

(65) Prior Publication Data

US 2021/0106383 A1 Apr. 15, 2021

Related U.S. Application Data

(63) Continuation of application No. 16/653,298, filed on Oct. 15, 2019, now Pat. No. 10,799,289.

(Continued)

(51) Int. Cl.
*A61B 18/14* (2006.01)
*A61L 24/00* (2006.01)
(Continued)

(52) U.S. Cl.
CPC ........ *A61B 18/1492* (2013.01); *A61L 24/001* (2013.01); *A61L 24/046* (2013.01); *A61M 5/007* (2013.01); *A61M 25/0082* (2013.01); *A61B 2017/00292* (2013.01); *A61B 2017/00362* (2013.01); *A61B 17/00491* (2013.01); *A61B 2018/00005* (2013.01);
(Continued)

(58) Field of Classification Search
CPC .......... A61B 18/1492; A61B 17/00491; A61B 2017/00292; A61B 2017/00362; A61B 2018/00005; A61B 2018/00434; A61B 2018/00577; A61B 2018/0212; A61L 24/001; A61L 24/046; A61L 2400/06; A61M 5/007; A61M 25/0082; A61M 2205/054; A61M 2205/3606
See application file for complete search history.

(56) References Cited

U.S. PATENT DOCUMENTS 4,443,340 A 4/1984 May et al.
5,116,315 A 5/1992 Capozzi et al.
(Continued)

FOREIGN PATENT DOCUMENTS

CN 106902394 6/2017
WO 92/16484 10/1992
(Continued)

OTHER PUBLICATIONS

Lee, Bae-Hoon, et al. "Synthesis and characterization of thermosensitive poly (organophosphazenes) with methoxy-poly (ethylene glycol) and alkylamines as side groups." Bulletin of the Korean Chemical Society 23.4 (2002): 549-554.

(Continued)

*Primary Examiner* — Michael F Peffley
*Assistant Examiner* — Bo Ouyang
(74) *Attorney, Agent, or Firm* — Meunier Carlin & Curfman LLC

(57) ABSTRACT

Disclosed are compositions, devices, systems, kits, and methods for neural ablation.

19 Claims, 5 Drawing Sheets

Related U.S. Application Data

(60) Provisional application No. 62/745,826, filed on Oct. 15, 2018, provisional application No. 62/745,831, filed on Oct. 15, 2018, provisional application No. 62/745,835, filed on Oct. 15, 2018, provisional application No. 62/745,973, filed on Oct. 15, 2018.

(51) Int. Cl.

| | | |
|---|---|---|
| *A61L 24/04* | (2006.01) | |
| *A61M 5/00* | (2006.01) | |
| *A61M 25/00* | (2006.01) | |
| A61B 17/00 | (2006.01) | |
| A61B 18/00 | (2006.01) | |
| A61B 18/02 | (2006.01) | |

(52) U.S. Cl.
CPC ........... *A61B 2018/00434* (2013.01); *A61B 2018/00577* (2013.01); *A61B 2018/0212* (2013.01); *A61L 2400/06* (2013.01); *A61M 2205/054* (2013.01); *A61M 2205/3606* (2013.01)

(56) References Cited

U.S. PATENT DOCUMENTS

| | | | |
|---|---|---|---|
| 5,242,910 A | 9/1993 | Damani | |
| 5,310,865 A | 5/1994 | Enomoto et al. | |
| 5,523,492 A | 6/1996 | Emanuele et al. | |
| 5,567,859 A | 10/1996 | Emanuele et al. | |
| 5,696,298 A | 12/1997 | Emanuele et al. | |
| 5,792,478 A | 8/1998 | Lawin et al. | |
| 5,800,711 A | 9/1998 | Reeve et al. | |
| 6,721,603 B2 | 4/2004 | Zabara et al. | |
| 6,761,824 B2 | 7/2004 | Reeve et al. | |
| 6,896,675 B2 | 5/2005 | Leung et al. | |
| 6,919,426 B2 | 7/2005 | Boone et al. | |
| 7,076,399 B2 | 7/2006 | Godara | |
| 7,163,536 B2 | 1/2007 | Godara | |
| 7,252,822 B2 | 8/2007 | Shelton et al. | |
| 7,258,688 B1 | 8/2007 | Shah et al. | |
| 7,294,127 B2 | 11/2007 | Leung et al. | |
| 7,306,596 B2 | 12/2007 | Hillier et al. | |
| 7,533,002 B2 | 5/2009 | Godara | |
| 7,596,469 B2 | 9/2009 | Godara | |
| 7,655,231 B2 | 2/2010 | Shelton et al. | |
| 7,824,404 B2 | 11/2010 | Godara et al. | |
| 8,043,287 B2 | 10/2011 | Conquergood et al. | |
| 8,187,268 B2 | 5/2012 | Godara et al. | |
| 8,361,063 B2 | 1/2013 | Godara | |
| 8,361,067 B2 | 1/2013 | Pellegrino et al. | |
| 8,409,218 B2 | 4/2013 | Schwartz et al. | |
| 8,518,036 B2 | 8/2013 | Leung et al. | |
| 8,740,897 B2 | 6/2014 | Leung et al. | |
| 8,834,416 B2 | 9/2014 | Sahatjian et al. | |
| 8,864,759 B2 | 10/2014 | Godara | |
| 8,882,755 B2 | 11/2014 | Leung et al. | |
| 8,951,249 B2 | 2/2015 | Godara et al. | |
| 9,017,709 B2 | 4/2015 | Griguol et al. | |
| 9,173,700 B2 | 11/2015 | Godara et al. | |
| 9,186,197 B2 | 11/2015 | McKay | |
| 9,265,559 B2 | 2/2016 | Godara et al. | |
| 9,364,281 B2 | 6/2016 | Lefler et al. | |
| 9,486,275 B2 | 11/2016 | Harrison et al. | |
| 2003/0180364 A1 | 9/2003 | Chen et al. | |
| 2004/0138237 A1 | 7/2004 | Shah | |
| 2004/0266983 A1 | 12/2004 | Reeve et al. | |
| 2005/0143678 A1 | 6/2005 | Schwarz et al. | |
| 2007/0027449 A1 | 2/2007 | Godara et al. | |
| 2008/0206187 A1 | 8/2008 | Exner et al. | |
| 2008/0247984 A1 | 10/2008 | Messersmith et al. | |
| 2008/0253987 A1 | 10/2008 | Rehor et al. | |
| 2010/0278839 A1 | 11/2010 | Powell et al. | |
| 2011/0034916 A1 | 2/2011 | Te et al. | |
| 2011/0052672 A1 | 3/2011 | Krishnan et al. | |
| 2011/0251545 A1* | 10/2011 | Duffy | A61L 27/14 604/522 |
| 2011/0256135 A1 | 10/2011 | Fraunhofer et al. | |
| 2013/0096552 A1* | 4/2013 | Brace | A61B 18/18 606/41 |
| 2013/0178866 A1 | 7/2013 | McDougal et al. | |
| 2014/0170136 A1 | 6/2014 | Gearing | |
| 2016/0317621 A1* | 11/2016 | Bright | A61B 90/30 |
| 2017/0007277 A1* | 1/2017 | Drapeau | A61B 17/320016 |
| 2017/0027635 A1 | 2/2017 | Harrison et al. | |
| 2018/0251505 A1* | 9/2018 | Jabbari | A61L 27/227 |

FOREIGN PATENT DOCUMENTS

| | | |
|---|---|---|
| WO | 2017/085630 | 5/2017 |
| WO | 2018/041981 | 3/2018 |

OTHER PUBLICATIONS

Merhige, John, A.; Pluromed, Inc. Announces FDA Approval for BackStop; Sep. 22, 2009, 3 pgs.

Search Report issued in GB Application No. GB1914907.9, dated Mar. 30, 2020.

Examination Report issued in GB1914907.9 dated Apr. 13, 2022. 6 pages.

Dumortier, G. et al., "A Review of Poloxamer 407 Pharmaceutical and Pharmacological Characteristics," Pharmaceutical Research, vol. 23, No. 12, 2709-2728 (2006).

Zhang, L. et al., "Effect of a poloxamer 407-based thermosensitive gel on minimization of the thermal injury to diaphragm during microwave ablation of the liver," World Journal of Gastroenterology, col. 23, No. 12, 2141-2148 (2017).

Zhu, Y. et al., "A novel injectable thermo-sensitive binary hydrogels system for facilitating endoscopic submucosal disssection procedure," United European Gastroenterology Journal, vol. 7, No. 6, 782-789 (2019).

* cited by examiner

Polymer can be dispensed through various introducer manifestations

COMPOSITIONS, SYSTEMS, KITS, AND METHODS FOR NEURAL ABLATION

CROSS REFERENCE TO RELATED APPLICATIONS

This application claims benefit of priority of U.S. Provisional Application Nos. 62/745,826, 62/745,831, 62/745,835, and 62/745,973, each of which is hereby incorporated by reference in its entirety.

BACKGROUND

Approximately 50 million Americans suffer with persistent (chronic) pain. The number of people suffering with chronic pain is higher than the number suffering from serious or terminal illnesses. Yet, unlike major illnesses, most chronic pain is untreated or under-treated. Pain surveys report that 42% of those experiencing chronic pain have such severe pain that they are unable to work, and 63% of pain sufferers are unable to engage in the routine activities of daily life. It has been estimated that among active workers, the loss of productivity from common pain syndromes costs over 60 billion dollars annually. In recent years, consumer advocacy, demographics, and advances in pain control technology have highlighted the clinical need for solutions and advanced the practice of pain management to a priority for healthcare providers.

Patients suffering from chronic pain often consume analgesics, opioids, and non-steroidal anti-inflammatory drugs to alleviate their symptoms. In spite of available pharmaceutical therapies, chronic pain may manifest itself to such a degree that the patient's quality of life is greatly diminished. In such instances, the ablation of nerves can be used to treat pain. Ablation can involve, for example, the heating of a tissue by the application of energy, in order to create a lesion; it is theorized that the lesioning of nerves renders them unable to transmit neural signals, thus eliminating nociceptive sensations therefrom. One common method of ablation involves the application of electrical energy from an electrode. Monopolar apparatuses use a grounding pad and a single electrode (or a group of electrodes at the same potential), whereby the electrical field is concentrated around the electrode(s) to generate heat within the tissue. Bipolar or multipolar apparatuses also exist, whereby the electrical current passes substantially between the electrodes, allowing a lesion to be created around each and, depending on the voltage or power used, extending between the electrodes.

While ablation procedures can be effective, the results can be temporary. Therefore, improved methods of treating pain, including methods which provide prolonged pain relief, are needed.

SUMMARY

Existing ablation procedures can provide patients with pain relief over a span of 12-24 months following ablation. However, in almost all cases, this relief is temporary. There are several speculative reasons for the return of pain; however, one likely cause is the regeneration of the proximal nerve perpendicular from the ablation site. Following catastrophic nerve damage, such as that inflicted during an ablation procedure, neurogenesis begins at the proximal nerve ablation site (referred to as a growth cone). Meanwhile, the distal nerve site degrades (a process referred to as Wallerian degradation). Loss of the distal nerve complicates proper regeneration of the nerve at the lesion site, leading to uncontrolled growth from the proximal end of the nerve. It is hypothesized that this uncontrolled growth is the underlying cause for the return of pain in the months and years following an ablation procedure. By modulating neural regeneration at the lesion site following ablation, uncontrolled nerve growth (and the accompanying return of pain) can be mitigated, extending the pain-relieving effect of conventional neural ablation procedures.

Accordingly, provided herein are methods for ameliorating pain in a subject in need thereof. The methods can comprise inserting an introducer cannula into the subject and positioning a distal end of the introducer cannula proximate a treatment site comprising a nerve that transmits a pain impulse; advancing an ablation probe through the introducer to a region proximate to the treatment site; ablating the nerve with the ablation probe, thereby forming a lesion on the nerve; retracting the ablation probe; and injecting a liquid composition through the introducer cannula and into the treatment site. Following injection, the liquid composition can form a polymeric matrix at the treatment site.

In some embodiments, the liquid composition can comprise a stimuli-responsive biocompatible polymer that forms a polymeric matrix (e.g., a solid or gel) at the treatment site upon injection into a physiological environment. In other embodiments, the liquid composition can comprise a cross-linkable biomaterial that crosslinks in situ at the treatment site to form a polymeric matrix upon injection into a physiological environment. In other embodiments, the liquid composition can comprise a heat-activated biocompatible polymer. In these embodiments, the liquid composition can be injected through the introducer cannula and into the treatment site prior to ablation of the nerve. Subsequently, the heat generated by the RF ablation probe can induce the heat-activated biocompatible polymer to form a polymeric matrix at the treatment site. In other embodiments, the liquid composition can comprise a non-erodible biocompatible material and a population of energy-absorbing particles. Once injected, the biocompatible material can form a matrix comprising the population of energy-absorbing particles dispersed therein at the treatment site. Once formed, the matrix at the lesion site can be addressed by externally applied energy, allowing the lesion site can be reheated remotely. This can be used to retreat (e.g., re-ablate or re-lesion) the nerve without the need for surgical access to the treatment site. Also provided are systems, kits, devices and compositions for practicing these methods, as summarized below.

Stimuli-Responsive Biocompatible Polymers

In some embodiments, the liquid composition can comprise a stimuli-responsive biocompatible polymer that forms a polymeric matrix (e.g., a solid or gel) at the treatment site upon injection into a physiological environment. In these embodiments, methods for ameliorating pain in a subject in need thereof can comprise inserting an introducer cannula into the subject and positioning a distal end of the introducer cannula proximate a treatment site comprising a nerve that transmits a pain impulse; advancing an ablation probe through the introducer to a region proximate to the treatment site; ablating the nerve with the ablation probe, thereby forming a lesion on the nerve; retracting the ablation probe; and injecting a liquid composition comprising a stimuli-responsive biocompatible polymer through the introducer cannula and into the treatment site. Upon injection into a physiological environment, the stimuli-responsive biocompatible polymer forms a polymeric matrix (e.g., a solid or gel) at the treatment site.

The polymeric matrix can substantially surround the lesion, thereby modulating neural regeneration at the lesion site. For example, the polymeric matrix can limit or prevent macrophages from accessing the lesion site. Macrophages secrete growth factors that drive neurogenesis at the proximal end of the nerve. By limiting and/or preventing the ability of macrophages to access the lesion site, the quantity of neural growth factors reaching the lesion site (and by extension nerve growth at the proximal end of the nerve) can be controlled. If desired, active agents to control nerve growth can also be incorporated in the polymeric matrix. In these embodiments, the polymeric matrix can function as a depot, providing for controlled, local delivering these active agents at the lesion site. Thus, neural regeneration at the lesion site can be guided and controlled using a polymeric matrix, thereby prolonging the pain-relieving effects of the neural ablation procedures.

The ablation probe can comprise any suitable ablation probe known in the art for use in neural ablation procedures. For example, in some cases, the ablation probe can comprise a radiofrequency (RF) ablation probe, and the ablating step comprises applying energy using the RF probe to ablate the nerve. In certain cases, the radiofrequency (RF) ablation probe is actively or passively cooled. In other examples, the ablation probe can comprise a cryogenic ablation probe, and the ablating step comprises cooling the nerve using the cryogenic ablation probe.

Likewise, the introducer cannula can comprise any suitable cannula sized and dimensioned to provide percutaneous access to the treatment site. Generally, the introducer comprises a central channel sized and configured to receive the ablation probe and the delivery tip of a syringe therethrough. If desired for delivery of a particular stimuli-responsive biocompatible material, the introducer cannula is actively or passively cooled during the ablation step, during the injection step, or any combination thereof.

The stimuli-responsive biocompatible polymer can comprise any suitable biocompatible polymer(s) that undergo a transition from a liquid to a solid or gel upon introduction into a physiological environment (e.g., in response to a change in temperature, a change in pH, a change in ionic strength, a change in solvent(s), or a combination thereof). In some cases, the stimuli-responsive biocompatible can be a polymer that undergoes a transition from a liquid to a gel or solid upon injection into an aqueous environment. In other cases, the stimuli-responsive biocompatible can be a polymer that undergoes a transition from a liquid to a gel or solid in response to an increase in temperature upon injection into a subject.

In certain embodiments, the liquid composition can exhibit a viscosity of less than 1000 cP at 4° C. (e.g., to facilitate injectability). Upon injection into a subject, the stimuli-responsive biocompatible polymer increases in viscosity to form a polymeric matrix that exhibits a viscosity of at least 25,000 cP at 37° C. (e.g., a viscosity of from 25,000 cP to 100,000 cP at 37° C.).

Examples of stimuli-responsive biocompatible materials are known in the art, and include, for example, polylactides, polyglycolides, polycaprolactones, polyanhydrides, polyamines, polyurethanes, polyesteramides, poly(alkylene oxides), polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrolidone, polyethylene glycol, polydimethylsiloxanes, polyhydroxycellulose, chitin, alginates, chitosan, hyaluronic acid, and copolymers, terpolymers and mixtures thereof In certain embodiments, the stimuli-responsive biocompatible polymer can comprise an inverse thermosensitive polymer (i.e., a polymer that undergoes a transition from a liquid to a gel or solid in response to an increase in temperature). For example, the inverse thermosensitive polymer can exhibit a transition temperature of from 10° C. to 37° C. In some cases, the inverse thermosensitive polymer can be a liquid at 4° C., and undergoes a transition from a liquid to a gel or solid upon an increase in temperature from 4° C. to 37° C. In some cases, the inverse thermosensitive polymer can be a liquid at 23° C., and undergoes a transition from a liquid to a gel or solid upon an increase in temperature from 23° C. to 37° C.

A number of suitable inverse thermosensitive polymers are known in the art, and suitable for use in conjunction with the methods described herein. In some examples, the inverse thermosensitive polymer can comprise a poly(alkylene oxide), such as a poly(alkylene oxide) block copolymer. In certain examples, the inverse thermosensitive polymer comprises a poloxamer, a poloxamine, or a combination thereof. For example, the inverse thermosensitive polymer can comprise poloxamer 407, poloxamer 188, poloxamer 234, poloxamer 237, poloxamer 338, poloxamine 1107, poloxamine 1307, or a combination thereof. In some embodiments, the inverse thermosensitive polymer can comprise poloxamer 407, poloxamer 188, or a combination thereof.

In certain embodiments, the inverse thermosensitive polymer can comprise (i) from 20% to 40% by weight of a first inverse thermosensitive polymer defined by Formula I below

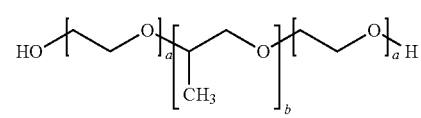

Formula I wherein a is an integer from 90 to 110 and b is an integer from 50 to 60, wherein the first inverse thermosensitive polymer has a molecular weight of from 9,500 Da to 15,000 Da, and wherein the first inverse thermosensitive polymer has a polyoxyethylene content of from 70% to 75%; and (ii) from 5% to 50% by weight of a second inverse thermosensitive polymer defined by Formula I below

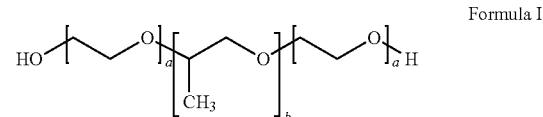

Formula I wherein a is an integer from 70 to 90 and b is an integer from 20 to 35, wherein the first inverse thermosensitive polymer has a molecular weight of from 7,500 Da to 10,000 Da, and wherein the first inverse thermosensitive polymer has a polyoxyethylene content of from 78% to 85%.

Upon injection, the stimuli-responsive biocompatible polymer forms a polymeric matrix. The polymeric matrix can be bioerodible. However, in some embodiments, the composition of the stimuli-responsive biocompatible polymer can be selected such that at least a portion of the polymeric matrix remains at the treatment site for an extended period of time prior to bioerosion. For example, in some embodiments, at least a portion of the polymeric matrix (e.g., at least 10% by mass, at least 25% by mass, at least 50% by mass, at least 75% by mass, at least 80% by mass, or at least 90% by mass) remains at the treatment site at least 24 hours (e.g., at least 48 hours, at least 72 hours, at least 96 hours, at least 120 hours, at least 144 hours, at least 1 week, at least 2 weeks, at least 3 weeks, or at least 4 weeks) after injection.

In some embodiments, the liquid composition can further comprise a solvent (e.g., water, saline, a buffer solution, DMSO, ethanol, methanol, glutaraldehyde, or combinations thereof).

In some embodiments, the liquid composition can further comprise an active agent. The active agent can be a therapeutic agent, a prophylactic agent, a diagnostic agent, or a combination thereof. For example, the active agent can comprise an anti-nerve growth factor, an anti-inflammatory agent, an analgesic, a contrast agent, a biomarker for monitoring clearance of the polymeric matrix, an NGF/TrkA pathway inhibitor, a substance P inhibitor, a CGRO inhibitor, extracellular matrix molecule proteins, or a combination thereof.

In some examples, the liquid composition can further comprise a contrast agent. Upon injection, the contrast agent can be retained (e.g., dissolved or dispersed in) the polymeric matrix. In these embodiments, methods can further comprise imaging the polymeric matrix (e.g., to confirm placement of the polymeric matrix at the treatment site, to monitor clearance of the polymeric matrix from the treatment site, or a combination thereof).

If desired, the liquid composition can comprise a unit dose of the liquid composition comprising the stimuli-responsive biocompatible polymer packaged within a syringe or other suitable implement that facilitates delivery of the liquid composition to the treatment site. The device can be sealed and sterilized so as to be ready for use by a physician while preforming a neural ablation procedure described herein.

Also provided are method for guiding neural tissue regeneration at a lesion site following neural ablation. These methods can comprise injecting a liquid composition comprising a stimuli-responsive biocompatible polymer at the lesion site, wherein upon injection into a physiological environment, the stimuli-responsive biocompatible polymer forms a polymeric matrix at the lesion site which modulates neural tissue regeneration.

Also provided are methods for prolonging the efficacy of a neural ablation procedure in a subject. These methods can comprise ablating a nerve with an ablation probe, thereby forming a lesion on the nerve; and applying a liquid composition comprising a stimuli-responsive biocompatible polymer to the lesion. Upon introduction into a physiological environment, the stimuli-responsive biocompatible polymer can form a polymeric matrix surrounding the lesion.

Also provided herein are systems and kits for use in conjunction with the methods described herein. For example, provided herein are systems for neural ablation that comprise (i) a liquid composition comprising a stimuli-responsive biocompatible polymer; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough.

As discussed above, the ablation probe can comprise any suitable ablation probe known in the art for use in neural ablation procedures. For example, in some cases, the ablation probe can comprise a radiofrequency (RF) ablation probe (e.g., a cooled RF probe). In other examples, the ablation probe can comprise a cryogenic ablation probe.

Likewise, the introducer cannula can comprise any suitable cannula sized and dimensioned to provide percutaneous access to the treatment site. Generally, the introducer comprises a central channel sized and configured to receive the ablation probe and the delivery tip of the syringe therethrough.

The syringe can further include a cooling mechanism (e.g., an insulating sheath, or a cooling pack) for regulating a temperature of the liquid composition within the volume of the barrel. The liquid composition can be any suitable composition described herein.

Also described are kits for performing a neural ablation procedure described herein. The kits can comprise the components of a system described herein (e.g., (i) a liquid composition comprising a stimuli-responsive biocompatible polymer; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough) enclosed within sterile packaging.

In some cases, the liquid composition can be loaded within the syringe. In other embodiments, the liquid composition can be packaged in a separate vial or container. In these embodiments, the liquid composition can be loaded within the syringe prior to use.

In some embodiments, the kit can further include a cooling mechanism (e.g., a physically activated cooling pack) for cooling the liquid composition prior to use.

In certain embodiments, the kit can comprise (i) from one to eight volumes of a liquid composition comprising a stimuli-responsive biocompatible polymer; (ii) from one to eight syringes, each syringe comprising a barrel defining a volume for containing the liquid composition, a distal end of the barrel including a delivery tip; and a plunger sized and configured to move within the volume of the barrel to convey the liquid composition through the delivery tip; (iii) from one to eight ablation probes; and (iv) from one to eight introducer cannulae, each introducer cannula comprising a central channel sized and configured to receive an ablation probe and a delivery tip therethrough.

Also provided herein are devices for guiding neural regeneration following ablation. The devices can comprise unit doses of a liquid composition comprising a stimuli-responsive biocompatible polymer packaged within a syringe or other suitable implement that facilitates delivery of the liquid composition to the treatment site. The device can be sealed and sterilized so as to be ready for use by a physician while preforming a neural ablation procedure described herein.

The syringe can comprise a barrel defining a volume containing from 1 mL to 10 mL (e.g., from 1 mL to 5 mL) of a liquid composition, a distal end of the barrel including a delivery tip; and a plunger sized and configured to move within the volume of the barrel to convey the liquid composition through the delivery tip. The liquid composition can comprise (i) from 20% to 40% by weight of a first inverse thermosensitive polymer defined by Formula I below

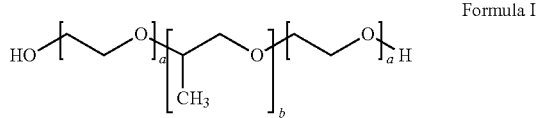

Formula I wherein a is an integer from 90 to 110 and b is an integer from 50 to 60, wherein the first inverse thermosensitive polymer has a molecular weight of from 9,500 Da to 15,000 Da, and wherein the first inverse thermosensitive polymer has a polyoxyethylene content of from 70% to 75%; and (ii) from 5% to 50% by weight of a second inverse thermosensitive polymer defined by Formula I below

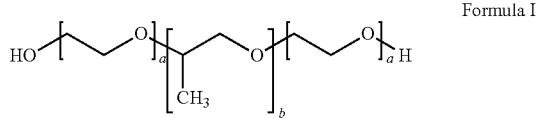

Formula I wherein a is an integer from 70 to 90 and b is an integer from 20 to 35, wherein the first inverse thermosensitive polymer has a molecular weight of from 7,500 Da to 10,000 Da, and wherein the first inverse thermosensitive polymer has a polyoxyethylene content of from 78% to 85%. The first inverse thermosensitive polymer and the second inverse thermosensitive polymer, in combination, can exhibit a transition temperature of from 10° C. to 37° C. The first inverse thermosensitive polymer and the second inverse thermosensitive polymer, in combination, can exhibit a viscosity of at least 25,000 at 37° C., such as a viscosity of from 25,000 to 100,000 cP at 37° C.

The liquid composition can be formulated so as to exhibit a viscosity of less than 1000 cP at 4° C. (e.g., to facilitate injectability).

In some embodiments, the liquid composition can further comprise a solvent (e.g., water, saline, a buffer solution, DMSO, ethanol, methanol, glutaraldehyde, or combinations thereof).

In some embodiments, the liquid composition can further comprise an active agent. The active agent can be a therapeutic agent, a prophylactic agent, a diagnostic agent, or a combination thereof. For example, the active agent can comprise an anti-nerve growth factor, an anti-inflammatory agent, an analgesic, a contrast agent, a biomarker for monitoring clearance of the polymeric matrix, an NGF/TrkA pathway inhibitor, or a combination thereof.

Crosslinkable Biomaterials

In some embodiments, the liquid composition can comprise a crosslinkable biomaterial that crosslinks in situ at the treatment site to form a polymeric matrix upon injection into a physiological environment. In these embodiments, methods for ameliorating pain in a subject in need thereof can comprise inserting an introducer cannula into the subject and positioning a distal end of the introducer cannula proximate a treatment site comprising a nerve that transmits a pain impulse; advancing an ablation probe through the introducer to a region proximate to the treatment site; ablating the nerve with the ablation probe, thereby forming a lesion on the nerve; retracting the ablation probe; and injecting a liquid composition comprising a crosslinkable biomaterial through the introducer cannula and into the treatment site. Upon injection into a physiological environment, the crosslinkable biomaterial crosslinks in situ at the treatment site to form a polymeric matrix.

The polymeric matrix can substantially surround the lesion, thereby modulating neural regeneration at the lesion site. For example, the polymeric matrix can limit or prevent macrophages from accessing the lesion site. Macrophages secrete growth factors that drive neurogenesis at the proximal end of the nerve. By limiting and/or preventing the ability of macrophages to access the lesion site, the quantity of neural growth factors reaching the lesion site (and by extension nerve growth at the proximal end of the nerve) can be controlled. If desired, active agents to control nerve growth can also be incorporated in the polymeric matrix. In these embodiments, the polymeric matrix can function as a depot, providing for controlled, local delivering these active agents at the lesion site. Thus, neural regeneration at the lesion site can be guided and controlled using a polymeric matrix, thereby prolonging the pain-relieving effects of the neural ablation procedures.

The ablation probe can comprise any suitable ablation probe known in the art for use in neural ablation procedures. For example, in some cases, the ablation probe can comprise a radiofrequency (RF) ablation probe, and the ablating step comprises applying energy using the RF probe to ablate the nerve. In certain cases, the radiofrequency (RF) ablation probe is actively or passively cooled. In other examples, the ablation probe can comprise a cryogenic ablation probe, and the ablating step comprises cooling the nerve using the cryogenic ablation probe.

Likewise, the introducer cannula can comprise any suitable cannula sized and dimensioned to provide percutaneous access to the treatment site. Generally, the introducer comprises a central channel sized and configured to receive the ablation probe and the delivery tip of a syringe therethrough.

In certain embodiments, the liquid composition can exhibit a viscosity of less than 1000 cP at 4° C. (e.g., to facilitate injectability). Upon injection into a subject, the crosslinkable biomaterial increases in viscosity to form a polymeric matrix that exhibits a viscosity of at least 25,000 cP at 37° C. (e.g., a viscosity of from 25,000 cP to 100,000 cP at 37° C.).

In some embodiments, the crosslinkable biomaterial comprises a first precursor molecule and a second precursor molecule.

For example, in some embodiments, the first precursor molecule can comprise an oligomer or polymer having one or more first reactive groups, each first reactive group comprising one or more pi bonds, and the second precursor molecule can comprise an oligomer or polymer having one or more second reactive groups, each second reactive group comprising one or more pi bonds. The first reactive group can be reactive with the second reactive group to form a covalent bond between the first precursor molecule and the second precursor molecule. For example, the first reactive group and the second reactive group can undergo a cycloaddition reaction.

In other embodiments, the first precursor molecule can comprise an oligomer or polymer having one or more nucleophilic groups, and the second precursor molecule can comprise an oligomer or polymer having one or more conjugated unsaturated groups. For example, the first precursor molecule can comprise a poly(alkylene oxide)-based oligomer or polymer (e.g., a poly(ethylene glycol)) having x nucleophilic groups, wherein x is an integer greater than or equal to 2 (e.g., an integer of from 2 to 8, such as an integer of from 2 to 6). The nucleophilic groups can be selected from the group consisting of sulfhydryl groups and amino groups. For example, the first precursor molecule can comprise pentaerythritol poly(ethylene glycol)ether tetrasulfhydryl. The second precursor molecule can comprise a biomacromolecule (e.g., a polysaccharide such as dextran or a derivative thereof) having y conjugated unsaturated groups, wherein y is an integer greater than or equal to 2 (e.g., an integer of from 2 to 100, such as from 2 to 25). The conjugated unsaturated groups can be selected from the group consisting of vinyl sulfone groups and acryl groups. For example, the second precursor molecule can comprise dextran vinyl sulfone.

Upon injection, the crosslinkable biomaterial forms a polymeric matrix. The polymeric matrix can be bioerodible. However, in some embodiments, the composition of the crosslinkable biomaterial can be selected such that at least a portion of the polymeric matrix remains at the treatment site for an extended period of time prior to bioerosion. For example, in some embodiments, at least a portion of the polymeric matrix (e.g., at least 10% by mass, at least 25% by mass, at least 50% by mass, at least 75% by mass, at least 80% by mass, or at least 90% by mass) remains at the treatment site at least 24 hours (e.g., at least 48 hours, at least 72 hours, at least 96 hours, at least 120 hours, at least 144 hours, at least 1 week, at least 2 weeks, at least 3 weeks, or at least 4 weeks) after injection.

In some embodiments, the liquid composition can further comprise a solvent (e.g., water, saline, a buffer solution, DMSO, ethanol, methanol, glutaraldehyde, or combinations thereof).

In some embodiments, the liquid composition can further comprise an active agent. The active agent can be a therapeutic agent, a prophylactic agent, a diagnostic agent, or a combination thereof. For example, the active agent can comprise an anti-nerve growth factor, an anti-inflammatory agent, an analgesic, a contrast agent, a biomarker for monitoring clearance of the polymeric matrix, an NGF/TrkA pathway inhibitor, a substance P inhibitor, a CGRO inhibitor, extracellular matrix molecule proteins, or a combination thereof.

In some examples, the liquid composition can further comprise a contrast agent. Upon injection, the contrast agent can be retained (e.g., dissolved or dispersed in) the polymeric matrix. In these embodiments, methods can further comprise imaging the polymeric matrix (e.g., to confirm placement of the polymeric matrix at the treatment site, to monitor clearance of the polymeric matrix from the treatment site, or a combination thereof).

If desired, the liquid composition can comprise a unit dose of the liquid composition comprising a crosslinkable biomaterial packaged within a syringe or other suitable implement that facilitates delivery of the liquid composition to the treatment site. The device can be sealed and sterilized so as to be ready for use by a physician while preforming a neural ablation procedure described herein.

Also provided are method for guiding neural tissue regeneration at a lesion site following neural ablation. These methods can comprise injecting a liquid composition comprising a crosslinkable biomaterial at the lesion site, wherein upon injection into a physiological environment, the crosslinkable biomaterial forms a polymeric matrix at the lesion site which modulates neural tissue regeneration.

Also provided are methods for prolonging the efficacy of a neural ablation procedure in a subject. These methods can comprise ablating a nerve with an ablation probe, thereby forming a lesion on the nerve; and applying a liquid composition comprising a crosslinkable biomaterial to the lesion. Upon introduction into a physiological environment, the crosslinkable biomaterial can form a polymeric matrix surrounding the lesion.

Also provided herein are systems and kits for use in conjunction with the methods described herein. For example, provided herein are systems for neural ablation that comprise (i) a crosslinkable biomaterial; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough.

Also provided are systems for neural ablation comprising: (i) a bicomponent crosslinkable biomaterial comprising a first precursor solution and a second precursor solution; (ii) a dual barrel syringe comprising a first barrel defining a volume for containing the first precursor solution, a distal end of the first barrel fluidly connected to a delivery tip; a second barrel defining a volume for containing the second precursor solution, a distal end of the second barrel fluidly connected to a delivery tip; and a plunger sized and configured to move within the volume of the first barrel and the volume of the second barrel to convey the first precursor solution and the second precursor solution through the delivery tip; (iii) an ablation probe; and (iv) an introducer cannula comprising a central channel sized and configured to receive the ablation probe and the delivery tip therethrough.

As discussed above, the ablation probe can comprise any suitable ablation probe known in the art for use in neural ablation procedures. For example, in some cases, the ablation probe can comprise a radiofrequency (RF) ablation probe (e.g., a cooled RF probe). In other examples, the ablation probe can comprise a cryogenic ablation probe.

Likewise, the introducer cannula can comprise any suitable cannula sized and dimensioned to provide percutaneous access to the treatment site. Generally, the introducer comprises a central channel sized and configured to receive the ablation probe and the delivery tip of the syringe therethrough.

Also described are kits for performing a neural ablation procedure described herein. The kits can comprise the components of a system described herein (e.g., (i) a liquid composition comprising a stimuli-responsive biocompatible polymer; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough; or (i) a bicomponent crosslinkable biomaterial comprising a first precursor solution and a second precursor solution; (ii) a dual barrel syringe comprising a first barrel defining a volume for containing the first precursor solution, a distal end of the first barrel fluidly connected to a delivery tip; a second barrel defining a volume for containing the second precursor solution, a distal end of the second barrel fluidly connected to a delivery tip; and a plunger sized and configured to move within the volume of the first barrel and the volume of the second barrel to convey the first precursor solution and the second precursor solution through the delivery tip; (iii) an ablation probe; and (iv) an introducer cannula comprising a central channel sized and configured to receive the ablation probe and the delivery tip therethrough) enclosed within sterile packaging.

In some cases, the liquid composition (or first precursor solution and second precursor solution) can be loaded within the syringe. In other embodiments, the liquid composition (or first precursor solution and second precursor solution) can be packaged in a separate vial or container. In these embodiments, the liquid composition (or first precursor solution and second precursor solution) can be loaded within the syringe prior to use.

In certain embodiments, the kit can comprise (i) from one to eight volumes of the crosslinkable biomaterial; (ii) from one to eight syringes; (iii) from one to eight ablation probes; and (iv) from one to eight introducer cannulae, each introducer cannula comprising a central channel sized and configured to receive an ablation probe and a delivery tip therethrough.

Heat-Activated Biocompatible Polymers

In some embodiments, the liquid composition can comprise a heat-activated biocompatible polymer. In these embodiments, methods for ameliorating pain in a subject in need thereof can comprise inserting an introducer cannula into the subject and positioning a distal end of the introducer cannula proximate a treatment site comprising a nerve that transmits a pain impulse; injecting a liquid composition comprising a heat-activated biocompatible polymer through the introducer cannula and into the treatment site; advancing a radiofrequency (RF) ablation probe through the introducer to a region proximate to the treatment site; and applying energy using the RF ablation probe to ablate the nerve, thereby forming a lesion on the nerve. The heat generated by the RF ablation probe induces the heat-activated biocompatible polymer to form a polymeric matrix at the treatment site.

The polymeric matrix can substantially surround the lesion, thereby modulating neural regeneration at the lesion site. For example, the polymeric matrix can limit or prevent macrophages from accessing the lesion site. Macrophages secrete growth factors that drive neurogenesis at the proximal end of the nerve. By limiting and/or preventing the ability of macrophages to access the lesion site, the quantity of neural growth factors reaching the lesion site (and by extension nerve growth at the proximal end of the nerve) can be controlled. If desired, active agents to control nerve growth can also be incorporated in the polymeric matrix. In these embodiments, the polymeric matrix can function as a depot, providing for controlled, local delivering these active agents at the lesion site. Thus, neural regeneration at the lesion site can be guided and controlled using a polymeric matrix, thereby prolonging the pain-relieving effects of the neural ablation procedures.

The ablation probe can comprise any suitable RF ablation probe known in the art for use in neural ablation procedures. In certain cases, the radiofrequency (RF) ablation probe is actively or passively cooled. Likewise, the introducer cannula can comprise any suitable cannula sized and dimensioned to provide percutaneous access to the treatment site. Generally, the introducer comprises a central channel sized and configured to receive the ablation probe and the delivery tip of a syringe therethrough. If desired for delivery of a particular heat-activated biocompatible material, the introducer cannula is actively or passively cooled during the ablation step, during the injection step, or any combination thereof.

The heat-activated biocompatible polymer can comprise any suitable biocompatible polymer(s) that undergo a transition from a liquid to a solid or gel upon heating with an RF ablation probe (e.g., when heated to a temperature of from 40° C. to 70° C.). The transition can be irreversible, such that once the heat-activated biocompatible polymer has been heated to form a solid or gel (a polymeric matrix), the resulting polymeric matrix remains a solid or liquid at physiological temperature (37° C.).

In certain embodiments, the liquid composition can exhibit a viscosity of less than 1000 cP at 4° C. (e.g., to facilitate injectability). Upon exposure to heat generated by the RF ablation probe (e.g., a temperature of from 40° C. to 70° C.), the heat-activated biocompatible polymer forms a polymeric matrix that exhibits a viscosity of at least 25,000 cP at 37° C. (e.g., a viscosity of from 25,000 cP to 100,000 cP at 37° C.).

The heat-activated biocompatible polymer can comprise any suitable biocompatible polymeric material which undergoes an irreversible transition from a liquid to a solid or gel at a temperature greater than physiological temperature (e.g., a temperature of from 40° C. to 70° C.). In some embodiments, the heat-activated biocompatible polymer can comprise any biocompatible polymeric material which undergoes a crosslinking reaction at a temperature greater than physiological temperature (e.g., a temperature of from 40° C. to 70° C.). For example, the heat-activated biocompatible polymer can comprise a crosslinkable polymer and a thermally activated crosslinker. The crosslinkable polymer can comprise, for example, a polymer selected from the group consisting of polylactides, polyglycolides, polycaprolactones, polyanhydrides, polyamines, polyurethanes, polyesteramides, poly(alkylene oxides), polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polydimethylsiloxanes, polyhydroxycellulose, chitin, alginates, chitosan, hyaluronic acid, and copolymers, terpolymers and mixtures thereof. The thermally activated crosslinker can comprise a crosslinking agent for the crosslinkable polymer encapsulated in a lipid vesicle. The lipid vesicle can be formulated to degrade at a temperature of from 40° C. to 70° C., allowing the crosslinking agent to be released locally to crosslink the crosslinkable polymer when the heat-activated biocompatible polymer is heated.

Upon heating, the heat-activated biocompatible polymer forms a polymeric matrix. The polymeric matrix can be bioerodible. However, in some embodiments, the composition of the heat-activated biocompatible polymer can be selected such that at least a portion of the polymeric matrix remains at the treatment site for an extended period of time prior to bioerosion. For example, in some embodiments, at least a portion of the polymeric matrix (e.g., at least 10% by mass, at least 25% by mass, at least 50% by mass, at least 75% by mass, at least 80% by mass, or at least 90% by mass) remains at the treatment site at least 24 hours (e.g., at least 48 hours, at least 72 hours, at least 96 hours, at least 120 hours, at least 144 hours, at least 1 week, at least 2 weeks, at least 3 weeks, or at least 4 weeks) after injection.

In some embodiments, the liquid composition can further comprise a solvent (e.g., water, saline, a buffer solution, DMSO, ethanol, methanol, glutaraldehyde, or combinations thereof).

In some embodiments, the liquid composition can further comprise an active agent. The active agent can be a therapeutic agent, a prophylactic agent, a diagnostic agent, or a combination thereof. For example, the active agent can comprise an anti-nerve growth factor, an anti-inflammatory agent, an analgesic, a contrast agent, a biomarker for monitoring clearance of the polymeric matrix, an NGF/TrkA pathway inhibitor, a substance P inhibitor, a CGRO inhibitor, extracellular matrix molecule proteins, or a combination thereof.

In some examples, the liquid composition can further comprise a contrast agent. Upon injection, the contrast agent can be retained (e.g., dissolved or dispersed in) the polymeric matrix. In these embodiments, methods can further comprise imaging the polymeric matrix (e.g., to confirm placement of the polymeric matrix at the treatment site, to monitor clearance of the polymeric matrix from the treatment site, or a combination thereof).

Also provided are methods for guiding neural tissue regeneration at a lesion site following neural ablation. These methods can comprise injecting a liquid composition comprising a heat-activated biocompatible polymer at a treatment site comprising a nerve that transmits a pain impulse, and applying energy using the RF ablation probe to ablate the nerve, thereby forming a lesion on the nerve. The heat generated by the RF ablation probe can induce the heat-activated biocompatible polymer to form a polymeric matrix at the treatment site which modulates neural tissue regeneration.

Also provided are methods for prolonging the efficacy of a neural ablation procedure in a subject. These methods can comprise introducing a liquid composition comprising a heat-activated biocompatible polymer at a treatment site comprising a nerve that transmits a pain impulse; and ablating the nerve with a radiofrequency (RF) ablation probe, thereby forming a lesion on the nerve. The heat generated by the RF ablation probe can induce the heat-activated biocompatible polymer to form a polymeric matrix surrounding the lesion.

Also provided herein are systems and kits for use in conjunction with the methods described herein. For example, provided herein are systems for neural ablation that comprise (i) a liquid composition comprising a heat-activated biocompatible polymer; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) a radiofrequency (RF) ablation probe; and (iv) an introducer cannula comprising a central channel sized and configured to receive the ablation probe and the delivery tip therethrough.

As discussed above, the RF ablation probe can comprise any suitable RF ablation probe known in the art for use in neural ablation procedures. For example, in some cases, the ablation probe can comprise a radiofrequency (RF) ablation probe (e.g., a cooled RF probe). Likewise, the introducer cannula can comprise any suitable cannula sized and dimensioned to provide percutaneous access to the treatment site. Generally, the introducer comprises a central channel sized and configured to receive the RF ablation probe and the delivery tip of the syringe therethrough. The liquid composition can be any suitable composition described herein.

Also described are kits for performing a neural ablation procedure described herein. The kits can comprise the components of a system described herein (e.g., (i) a liquid composition comprising a heat-activated biocompatible polymer; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an RF ablation probe; and (iv) an introducer cannula comprising a central channel sized and configured to receive the ablation probe and the delivery tip therethrough) enclosed within sterile packaging.

In some cases, the liquid composition can be loaded within the syringe. For example, the liquid composition can comprise unit doses of a liquid composition comprising a heat-activated biocompatible polymer packaged within a syringe or other suitable implement that facilitates delivery of the liquid composition to the treatment site. The device can be sealed and sterilized so as to be ready for use by a physician while preforming a neural ablation procedure described herein. In other embodiments, the liquid composition can be packaged in a separate vial or container. In these embodiments, the liquid composition can be loaded within the syringe prior to use.

In certain embodiments, the kit can comprise (i) from one to eight volumes of a liquid composition comprising a heat-activated biocompatible polymer; (ii) from one to eight syringes, each syringe comprising a barrel defining a volume for containing the liquid composition, a distal end of the barrel including a delivery tip; and a plunger sized and configured to move within the volume of the barrel to convey the liquid composition through the delivery tip; (iii) from one to eight RF ablation probes; and (iv) from one to eight introducer cannulae, each introducer cannula comprising a central channel sized and configured to receive an ablation probe and a delivery tip therethrough.

Non-Erodible Biocompatible Material and Energy-Absorbing Particles

In some embodiments, the liquid composition can comprise a non-erodible biocompatible material and a population of energy-absorbing particles. Once injected, the biocompatible material can form a matrix comprising the population of energy-absorbing particles dispersed therein at the treatment site.

As discussed above, existing ablation procedures can provide patients with pain relief over a span of 12-24 months following ablation. Typically, a subsequent percutaneous ablation procedure is then required to relieve the pain once it returns. However, by providing an implant (also referred to herein as a matrix) at the lesion site that can be addressed by externally applied energy, the lesion site can be reheated remotely. This can allow for retreatment (e.g., re-ablation or re-lesioning) of the nerve without the need for surgical access to the treatment site. Further, the implant can also modulate neural regeneration at the lesion site following ablation, uncontrolled nerve growth (and the accompanying return of pain) can be mitigated, extending the pain-relieving effect of conventional neural ablation procedures.

Accordingly, provided herein are methods for ameliorating pain in a subject in need thereof. The methods can comprise inserting an introducer cannula into the subject and positioning a distal end of the introducer cannula proximate a treatment site comprising a nerve that transmits a pain impulse; advancing an ablation probe through the introducer to a region proximate to the treatment site; ablating the nerve with the ablation probe, thereby forming a lesion on the nerve; and injecting a liquid composition comprising a non-erodible biocompatible material and a population of energy-absorbing particles through the introducer cannula and into the treatment site. Once injected, the biocompatible material forms a matrix comprising the population of energy-absorbing particles dispersed therein at the treatment site.

The matrix can substantially surround the lesion, thereby modulating neural regeneration at the lesion site. For example, the matrix can limit or prevent macrophages from accessing the lesion site. Macrophages secrete growth factors that drive neurogenesis at the proximal end of the nerve. By limiting and/or preventing the ability of macrophages to access the lesion site, the quantity of neural growth factors reaching the lesion site (and by extension nerve growth at the proximal end of the nerve) can be controlled. If desired, active agents to control nerve growth can also be incorporated in the polymeric matrix. In these embodiments, the polymeric matrix can function as a depot, providing for controlled, local delivering these active agents at the lesion site. Thus, neural regeneration at the lesion site can be guided and controlled using a matrix, thereby prolonging the pain-relieving effects of the neural ablation procedures.

Further, the matrix includes energy-absorbing particles dispersed therein. External energy (e.g., from outside the subject's body) can be applied to the matrix. The energy-absorbing particles in the matrix can absorb the external energy, and release heat locally at the treatment site. The external energy can be, for example, infrared light, microwave radiation, radiowaves, alternating magnetic fields, or acoustic energy such as ultrasonic waves. In some cases, the external energy can applied to the matrix material following return of the pain in the subject. This can be, for example, from 6 months two 2 years following ablation of the nerve (or longer or shorter depending on factors such as the rate at which the pain returns, and the clearance time for the matrix at the treatment site). The heat released can be effective to heat the nerve to ameliorate pain in the subject (e.g., to re-ablate or re-lesion the nerve). For example, in some embodiments, the heat released is effective to heat the nerve to a temperature of at least 60° C. (e.g., at least 70° C.).

The ablation probe can comprise any suitable RF ablation probe known in the art for use in neural ablation procedures. In certain cases, the radiofrequency (RF) ablation probe is actively or passively cooled. Likewise, the introducer cannula can comprise any suitable cannula sized and dimensioned to provide percutaneous access to the treatment site. Generally, the introducer comprises a central channel sized and configured to receive the ablation probe and the delivery tip of a syringe therethrough. If desired for delivery of a particular heat-activated biocompatible material, the introducer cannula is actively or passively cooled during the ablation step, during the injection step, or any combination thereof.

The biocompatible material can comprise any suitable biocompatible polymer(s) that undergo a transition from a liquid to a solid or gel upon injection into the body. The transition can be irreversible, such that the resulting polymeric matrix remains a solid or liquid at physiological temperature (37° C.).

In certain embodiments, the liquid composition can exhibit a viscosity of less than 1000 cP at 4° C. (e.g., to facilitate injectability). Upon injection, the biocompatible material forms a matrix that exhibits a viscosity of at least 25,000 cP at 37° C. (e.g., a viscosity of from 25,000 cP to 100,000 cP at 37° C.).

Examples of suitable materials include, for example, polymer particles which comprise a complex of crosslinked sodium polyacrylate with a copolymer of polyvinyl alcohol-polyvinyl acetate (e.g., a Vantris-type formulation), polydimethylsiloxane (e.g., such as compositions sold under the tradename MARCOPLASTIQUE®), injectable calcium phosphate cements, and crosslinkable polyurethanes (e.g., a lysine-derived polyurethane).

Upon heating, the biocompatible material forms a matrix. The matrix can be non-bioerodible (meaning that at least a portion of the matrix remains at the lesion site for a period of one year prior to bioerosion). For example, in some embodiments, at least a portion of the matrix (e.g., at least 10% by mass, at least 25% by mass, at least 50% by mass, at least 75% by mass, at least 80% by mass, or at least 90% by mass) remains at the treatment site at least 12 months after injection. In some embodiments, at least a portion of the matrix (e.g., at least 10% by mass, at least 25% by mass, at least 50% by mass, at least 75% by mass, at least 80% by mass, or at least 90% by mass) remains at the treatment site at least 18 months after injection. In some embodiments, at least a portion of the matrix (e.g., at least 10% by mass, at least 25% by mass, at least 50% by mass, at least 75% by mass, at least 80% by mass, or at least 90% by mass) remains at the treatment site at least 24 months after injection.

In some embodiments, the liquid composition can further comprise a solvent (e.g., water, saline, a buffer solution, DMSO, ethanol, methanol, glutaraldehyde, or combinations thereof).

In some embodiments, the liquid composition can further comprise an active agent. The active agent can be a therapeutic agent, a prophylactic agent, a diagnostic agent, or a combination thereof. For example, the active agent can comprise an anti-nerve growth factor, an anti-inflammatory agent, an analgesic, a contrast agent, a biomarker for monitoring clearance of the polymeric matrix, an NGF/TrkA pathway inhibitor, a substance P inhibitor, a CGRO inhibitor, extracellular matrix molecule proteins, or a combination thereof.

In some examples, the liquid composition can further comprise a contrast agent. Upon injection, the contrast agent can be retained (e.g., dissolved or dispersed in) the polymeric matrix. In these embodiments, methods can further comprise imaging the polymeric matrix (e.g., to confirm placement of the polymeric matrix at the treatment site, to monitor clearance of the polymeric matrix from the treatment site, or a combination thereof).

Also provided herein are systems and kits for use in conjunction with the methods described herein. For example, provided herein are systems for neural ablation that comprise (i) a liquid composition comprising a non-erodible biocompatible material and a population of energy-absorbing particles; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough.

As discussed above, the ablation probe can comprise any suitable ablation probe known in the art for use in neural ablation procedures. For example, in some cases, the ablation probe can comprise a radiofrequency (RF) ablation probe (e.g., a cooled RF probe). In other examples, the ablation probe can comprise a cryogenic ablation probe.

Likewise, the introducer cannula can comprise any suitable cannula sized and dimensioned to provide percutaneous access to the treatment site. Generally, the introducer comprises a central channel sized and configured to receive the ablation probe and the delivery tip of the syringe therethrough.

Also described are kits for performing a neural ablation procedure described herein. The kits can comprise the components of a system described herein (e.g., (i) a liquid composition comprising a non-erodible biocompatible material and a population of energy-absorbing particles; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough) enclosed within sterile packaging.

In some cases, the liquid composition can be loaded within the syringe. For example, the liquid composition can comprise unit doses of a liquid composition comprising a biocompatible material and particles packaged within a syringe or other suitable implement that facilitates delivery of the liquid composition to the treatment site. The device can be sealed and sterilized so as to be ready for use by a physician while preforming a neural ablation procedure described herein. In other embodiments, the liquid composition can be packaged in a separate vial or container. In these embodiments, the liquid composition can be loaded within the syringe prior to use.

In certain embodiments, the kit can comprise (i) from one to eight volumes of a liquid composition comprising a non-erodible biocompatible material and a population of energy-absorbing particles; (ii) from one to eight syringes, each syringe comprising a barrel defining a volume for containing the liquid composition, a distal end of the barrel including a delivery tip; and a plunger sized and configured to move within the volume of the barrel to convey the liquid composition through the delivery tip; (iii) from one to eight ablation probes; and (iv) from one to eight introducer cannulae, each introducer cannula comprising a central channel sized and configured to receive an ablation probe and a delivery tip therethrough.

DESCRIPTION OF DRAWINGS

FIG. 7A shows an ablation image of a CRF treated nerve at Day 0. FIG. 7B shows an ablation image of a CRF treated nerve at Day 7. FIG. 7C shows an ablation image of CRF treated nerve with the addition of TA 3 at Day 7. FIG. 7D shows an ablation image of CRF treated nerve with the addition of TA 3 at Day 14.

DETAILED DESCRIPTION

Definitions

Figure 1:
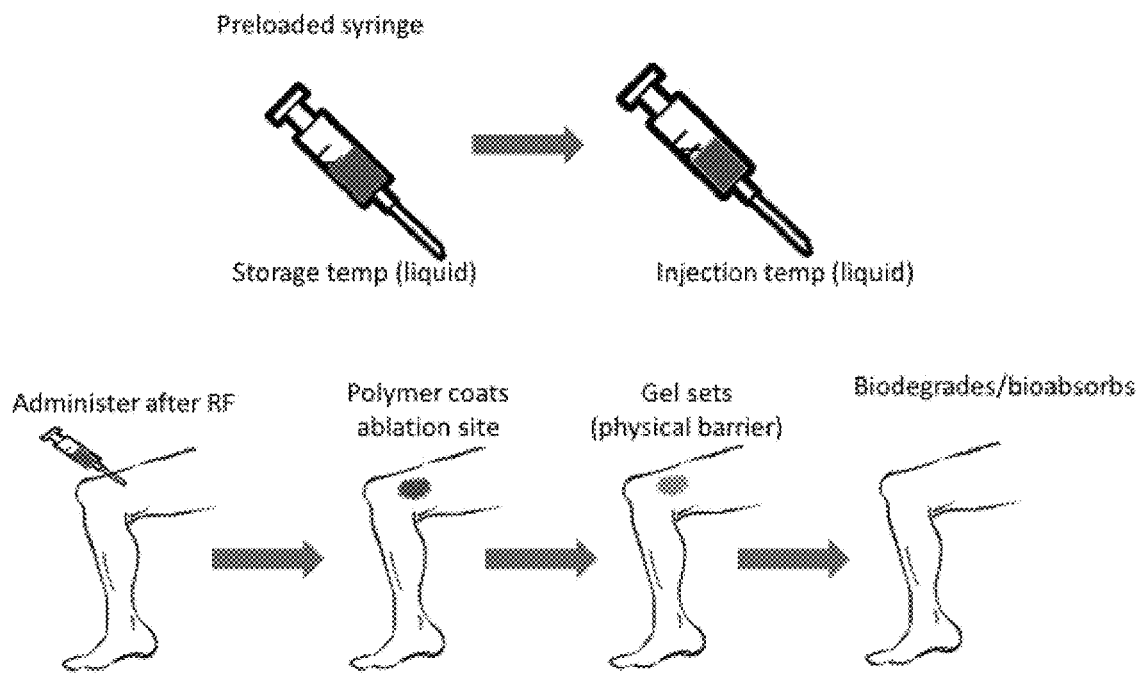
FIG. 1 is a simplified conceptual illustration of methods described herein
Figure 2:
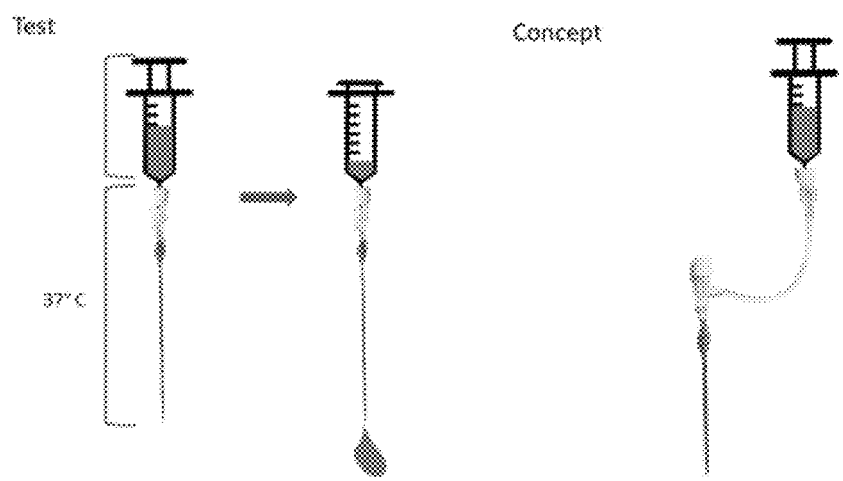
FIG. 2 is a schematic illustration showing injection of an example liquid composition through example introducers.

The terms "ablation" and "neural ablation" are used herein to broadly refer to a variety of accepted techniques (radiofrequency, microwave, cryoablation, laser interstitial and high-intensity focused ultrasound) for the destruction of one or more axons of a target nerve so as to result in a nerve blockade in which conduction or propagation of action potentials in the target nerve is attenuated or abolished, either reversibly or permanently, as evidenced by the attenuation or abolition of sensation normally mediated by the nerve or weakness or paralysis of the body tissue innervated by the target nerve lasting more than a week, more than two weeks, or more than a month.

The term "proximity to" as used herein refers to placing an element next to, or in a position near to, or in contact with another element or anatomical structure or tissue.

The term "pain" as used herein, unless specifically noted otherwise, is meant to encompass pain of any duration and frequency, including, but not limited to, acute pain, chronic pain, intermittent pain, and the like. Causes of pain may be identifiable or unidentifiable. Where identifiable, the origin of pain may be, for example, of malignant, non-malignant, infectious, non-infectious, or autoimmune origin. Of particular interest is the management of pain associated with disorders, diseases, or conditions that require long-term therapy, e.g., chronic and/or persistent diseases or conditions for which therapy involves treatment over a period of several days (e.g., about 3 days to 10 days), to several weeks (e.g., about 2 weeks or 4 weeks to 6 weeks), to several months or years, up to including the remaining lifetime of the subject. Pain includes all types of clinical pain, including but not limited to, nociceptive pain, pathological pain, neuropathic pain, somatic pain, cutaneous pain, chronic pain syndrome, referred pain, radicular pain, breakthrough pain or incidence pain, phantom limb pain, intractable pain and idiopathic pain, as defined in Hawthorn and Redmond, Pain: causes and managements, (Blackwell Science, Ed).

The term "inverse thermosensitive" refers to the property of a polymer wherein gelation and/or solidification (precipitation) takes place upon an increase in temperature, rather than a decrease in temperature. The term "transition temperature" refers to the temperature or temperature range at which gelation and/or solidification (precipitation) of an inverse thermosensitive polymer occurs.

The term "inverse thermosensitive polymer" as used herein refers to a polymer that is a liquid and/or is soluble in water at first temperature below body temperature (e.g., 4° C. or 23° C.), but which forms a solid or gel or at least partially phase-separates out of water, at physiological temperature (e.g., 37° C.). Examples of inverse thermosensitive polymers include poloxamer 407 (commercially available under the tradename PLURONIC® F127), poloxamer 188 (commercially available under the tradename PLURONIC® F68), poly(N-isopropylacrylamide), poly(methyl vinyl ether), poly(N-vinylcaprolactam), and certain poly(organophosphazenes). Such materials are described in *Bull. Korean Chem. Soc.* 2002, 23, 549-554, which is hereby incorporated by reference in its entirety.

The term "biocompatible", as used herein, refers to having the property of being biologically compatible by not producing a toxic, injurious, or immunological response in living tissue.

The term "poloxamer" denotes a symmetrical block copolymer, consisting of a core of PPG polyoxyethylated to both its terminal hydroxyl groups, i.e. conforming to the interchangeable generic formula $(PEG)_X$-$(PPG)_Y$-$(PEG)_X$ and $(PEO)_X$-$(PPO)_Y$-$(PEO)_X$. Each poloxamer name ends with an arbitrary code number, which is related to the average numerical values of the respective monomer units denoted by X and Y.

The term "poloxamine" denotes a polyalkoxylated symmetrical block copolymer of ethylene diamine conforming to the general type $[(PEG)_X$-$(PPG)_Y]_2$—$NCH_2CH_2N$—$[(PPG)_Y$-$(PEG)_X]_2$. Each Poloxamine name is followed by an arbitrary code number, which is related to the average numerical values of the respective monomer units denoted by X and Y.

The phrase "polydispersity index" refers to the ratio of the "weight average molecular weight" to the "number average molecular weight" for a particular polymer; it reflects the distribution of individual molecular weights in a polymer sample.

The phrase "weight average molecular weight" refers to a particular measure of the molecular weight of a polymer. The weight average molecular weight is calculated as follows: determine the molecular weight of a number of polymer molecules; add the squares of these weights; and then divide by the total weight of the molecules.

The phrase "number average molecular weight" refers to a particular measure of the molecular weight of a polymer. The number average molecular weight is the common average of the molecular weights of the individual polymer molecules. It is determined by measuring the molecular weight of n polymer molecules, summing the weights, and dividing by n.

Methods

Described herein are methods for ameliorating pain in a subject in need thereof. The methods can comprise inserting an introducer cannula into the subject and positioning a distal end of the introducer cannula proximate a treatment site comprising a nerve that transmits a pain impulse; advancing an ablation probe through the introducer to a region proximate to the treatment site; ablating the nerve with the ablation probe, thereby forming a lesion on the nerve; retracting the ablation probe; and injecting a liquid composition comprising a stimuli-responsive biocompatible polymer through the introducer cannula and into the treatment site.

Upon injection into a physiological environment, the stimuli-responsive biocompatible polymer forms a polymeric matrix (e.g., a solid or gel) at the treatment site. In some embodiments, the biocompatible polymers—and by extension the resulting polymeric matrix—are bioerodible, i.e., they gradually hydrolyze, dissolve, physically erode, or otherwise disintegrate within the aqueous fluids of a subject's body. Generally, the polymers bioerode as a result of hydrolysis or physical erosion, although the primary bioerosion process is typically hydrolysis. However, in some embodiments, the composition of the stimuli-responsive biocompatible polymer can be selected such that at least a portion of the polymeric matrix remains at the treatment site for an extended period of time prior to bioerosion. For example, in some embodiments, at least a portion of the polymeric matrix (e.g., at least 10% by mass, at least 25% by mass, at least 50% by mass, at least 75% by mass, at least 80% by mass, or at least 90% by mass) remains at the treatment site at least 24 hours (e.g., at least 48 hours, at least 72 hours, at least 96 hours, at least 120 hours, at least 144 hours, at least 1 week, at least 2 weeks, at least 3 weeks, or at least 4 weeks) after injection.

The polymeric matrix can substantially surround the lesion, thereby modulating neural regeneration at the lesion site. For example, the polymeric matrix can limit or prevent macrophages from accessing the lesion site. Macrophages secrete growth factors that drive neurogenesis at the proximal end of the nerve. By limiting and/or preventing the ability of macrophages to access the lesion site, the quantity of neural growth factors reaching the lesion site (and by extension nerve growth at the proximal end of the nerve) can be controlled. If desired, active agents to control nerve growth can also be incorporated in the polymeric matrix. In these embodiments, the polymeric matrix can function as a depot, providing for controlled, local delivering these active agents at the lesion site. Thus, neural regeneration at the lesion site can be guided and controlled using a polymeric matrix, thereby prolonging the pain-relieving effects of the neural ablation procedures.

Also provided are methods for ameliorating pain in a subject in need thereof that comprise inserting an introducer cannula into the subject and positioning a distal end of the introducer cannula proximate a treatment site comprising a nerve that transmits a pain impulse; advancing an ablation probe through the introducer to a region proximate to the treatment site; ablating the nerve with the ablation probe, thereby forming a lesion on the nerve; retracting the ablation probe; and injecting a liquid composition comprising a crosslinkable biomaterial through the introducer cannula and into the treatment site.

Upon injection into a physiological environment, the crosslinkable biomaterial crosslinks in situ at the treatment site to form a polymeric matrix. In some embodiments, the crosslinkable biomaterial—and by extension the resulting polymeric matrix—are bioerodible, i.e., they gradually hydrolyze, dissolve, physically erode, or otherwise disintegrate within the aqueous fluids of a subject's body. Generally, the polymers bioerode as a result of hydrolysis or physical erosion, although the primary bioerosion process is typically hydrolysis. However, in some embodiments, the composition of the crosslinkable biomaterial can be selected such that at least a portion of the polymeric matrix remains at the treatment site for an extended period of time prior to bioerosion. For example, in some embodiments, at least a portion of the polymeric matrix (e.g., at least 10% by mass, at least 25% by mass, at least 50% by mass, at least 75% by mass, at least 80% by mass, or at least 90% by mass) remains at the treatment site at least 24 hours (e.g., at least 48 hours, at least 72 hours, at least 96 hours, at least 120 hours, at least 144 hours, at least 1 week, at least 2 weeks, at least 3 weeks, or at least 4 weeks) after injection.

The polymeric matrix can substantially surround the lesion, thereby modulating neural regeneration at the lesion site. For example, the polymeric matrix can limit or prevent macrophages from accessing the lesion site. Macrophages secrete growth factors that drive neurogenesis at the proximal end of the nerve. By limiting and/or preventing the ability of macrophages to access the lesion site, the quantity of neural growth factors reaching the lesion site (and by extension nerve growth at the proximal end of the nerve) can be controlled. If desired, active agents to control nerve growth can also be incorporated in the polymeric matrix. In these embodiments, the polymeric matrix can function as a depot, providing for controlled, local delivering these active agents at the lesion site. Thus, neural regeneration at the lesion site can be guided and controlled using a polymeric matrix, thereby prolonging the pain-relieving effects of the neural ablation procedures.

Also provided are methods for ameliorating pain in a subject in need thereof that comprise inserting an introducer cannula into the subject and positioning a distal end of the introducer cannula proximate a treatment site comprising a nerve that transmits a pain impulse; injecting a liquid composition comprising a heat-activated biocompatible polymer through the introducer cannula and into the treatment site; advancing a radiofrequency (RF) ablation probe through the introducer to a region proximate to the treatment site; and applying energy using the RF ablation probe to ablate the nerve, thereby forming a lesion on the nerve. The heat generated by the RF ablation probe induces the heat-activated biocompatible polymer to form a polymeric matrix at the treatment site.

In some embodiments, the biocompatible polymers—and by extension the resulting polymeric matrix—are bioerodible, i.e., they gradually hydrolyze, dissolve, physically erode, or otherwise disintegrate within the aqueous fluids of a subject's body. Generally, the polymers bioerode as a result of hydrolysis or physical erosion, although the primary bioerosion process is typically hydrolysis. However, in some embodiments, the composition of the heat-activated biocompatible polymer can be selected such that at least a portion of the polymeric matrix remains at the treatment site for an extended period of time prior to bioerosion. For example, in some embodiments, at least a portion of the polymeric matrix (e.g., at least 10% by mass, at least 25% by mass, at least 50% by mass, at least 75% by mass, at least 80% by mass, or at least 90% by mass) remains at the treatment site at least 24 hours (e.g., at least 48 hours, at least 72 hours, at least 96 hours, at least 120 hours, at least 144 hours, at least 1 week, at least 2 weeks, at least 3 weeks, or at least 4 weeks) after injection.

The polymeric matrix can substantially surround the lesion, thereby modulating neural regeneration at the lesion site. For example, the polymeric matrix can limit or prevent macrophages from accessing the lesion site. Macrophages secrete growth factors that drive neurogenesis at the proximal end of the nerve. By limiting and/or preventing the ability of macrophages to access the lesion site, the quantity of neural growth factors reaching the lesion site (and by extension nerve growth at the proximal end of the nerve) can be controlled. If desired, active agents to control nerve growth can also be incorporated in the polymeric matrix. In these embodiments, the polymeric matrix can function as a depot, providing for controlled, local delivering these active agents at the lesion site. Thus, neural regeneration at the lesion site can be guided and controlled using a polymeric matrix, thereby prolonging the pain-relieving effects of the neural ablation procedures.

Also provided are methods for ameliorating pain in a subject in need thereof that comprise inserting an introducer cannula into the subject and positioning a distal end of the introducer cannula proximate a treatment site comprising a nerve that transmits a pain impulse; advancing an ablation probe through the introducer to a region proximate to the treatment site; ablating the nerve with the ablation probe, thereby forming a lesion on the nerve; and injecting a liquid composition comprising a non-erodible biocompatible material and a population of energy-absorbing particles through the introducer cannula and into the treatment site. Once injected, the biocompatible material forms a matrix comprising the population of energy-absorbing particles dispersed therein at the treatment site.

In some embodiments, the biocompatible material—and by extension the resulting matrix—is not bioerodible, i.e., at least a portion of the matrix remains at the lesion site for a period of one year prior to bioerosion. For example, in some embodiments, at least a portion of the matrix (e.g., at least 10% by mass, at least 25% by mass, at least 50% by mass, at least 75% by mass, at least 80% by mass, or at least 90% by mass) remains at the treatment site at least 12 months after injection. In some embodiments, at least a portion of the matrix (e.g., at least 10% by mass, at least 25% by mass, at least 50% by mass, at least 75% by mass, at least 80% by mass, or at least 90% by mass) remains at the treatment site at least 18 months after injection. In some embodiments, at least a portion of the matrix (e.g., at least 10% by mass, at least 25% by mass, at least 50% by mass, at least 75% by mass, at least 80% by mass, or at least 90% by mass) remains at the treatment site at least 24 months after injection.

The matrix can substantially surround the lesion, thereby modulating neural regeneration at the lesion site. For example, the matrix can limit or prevent macrophages from accessing the lesion site. Macrophages secrete growth factors that drive neurogenesis at the proximal end of the nerve. By limiting and/or preventing the ability of macrophages to access the lesion site, the quantity of neural growth factors reaching the lesion site (and by extension nerve growth at the proximal end of the nerve) can be controlled. If desired, active agents to control nerve growth can also be incorporated in the polymeric matrix. In these embodiments, the polymeric matrix can function as a depot, providing for controlled, local delivering these active agents at the lesion site. Thus, neural regeneration at the lesion site can be guided and controlled using a matrix, thereby prolonging the pain-relieving effects of the neural ablation procedures.

Further, the matrix includes energy-absorbing particles dispersed therein. External energy (e.g., from outside the subject's body) can be applied to the matrix. The energy-absorbing particles in the matrix can absorb the external energy, and release heat locally at the treatment site. The external energy can be, for example, infrared light, microwave radiation, radiowaves, alternating magnetic fields, or acoustic energy such as ultrasonic waves. In some cases, the external energy can applied to the matrix material following return of the pain in the subject. This can be, for example, from 6 months two 2 years following ablation of the nerve (or longer or shorter depending on factors such as the rate at which the pain returns, and the clearance time for the matrix at the treatment site). The heat released can be effective to heat the nerve to ameliorate pain in the subject (e.g., to re-ablate or re-lesion the nerve). For example, in some embodiments, the heat released is effective to heat the nerve to a temperature of at least 60° C. (e.g., at least 70° C.).

Liquid Compositions

In some embodiments, the liquid composition can comprise a stimuli-responsive biocompatible polymer that forms a polymeric matrix (e.g., a solid or gel) at the treatment site upon injection into a physiological environment. In other embodiments, the liquid composition can comprise a crosslinkable biomaterial that crosslinks in situ at the treatment site to form a polymeric matrix upon injection into a physiological environment. In other embodiments, the liquid composition can comprise a heat-activated biocompatible polymer. In these embodiments, the liquid composition can be injected through the introducer cannula and into the treatment site prior to ablation of the nerve. Subsequently, the heat generated by the RF ablation probe can induce the heat-activated biocompatible polymer to form a polymeric matrix at the treatment site. In other embodiments, the liquid composition can comprise a non-erodible biocompatible material and a population of energy-absorbing particles. Once injected, the biocompatible material can form a matrix comprising the population of energy-absorbing particles dispersed therein at the treatment site. Once formed, the matrix at the lesion site can be addressed by externally applied energy, allowing the lesion site can be reheated remotely. This can be used to retreat (e.g., re-ablate or re-lesion) the nerve without the need for surgical access to the treatment site.

Stimuli-Responsive Biocompatible Polymers

In some embodiments, liquid compositions can include a stimuli-responsive biocompatible polymer. The stimuli-responsive biocompatible polymer can comprise any suitable biocompatible polymer(s) that undergo a transition from a liquid to a solid or gel upon introduction into a physiological environment (e.g., in response to a change in temperature, a change in pH, a change in ionic strength, a change in solvent(s), or a combination thereof). In some cases, the stimuli-responsive biocompatible can be a polymer that undergoes a transition from a liquid to a gel or solid upon injection into an aqueous environment. In other cases, the stimuli-responsive biocompatible can be a polymer that undergoes a transition from a liquid to a gel or solid in response to an increase in temperature upon injection into a subject.

In certain embodiments, the liquid composition can exhibit a viscosity of less than 1000 cP at 4° C. (e.g., to facilitate injectability). For example, in some embodiments, the quid composition can exhibit a viscosity of less than 500 cP, less than 250 cP, or less than 100 cP at 4° C. Upon injection into a subject, the stimuli-responsive biocompatible polymer increases in viscosity to form a polymeric matrix that exhibits a viscosity of at least 25,000 cP at 37° C. (e.g., a viscosity of from 25,000 cP to 100,000 cP at 37° C.).

Examples of suitable stimuli-responsive biocompatible polymers include, but are not limited to, polylactides (e.g., poly(lactic acid) (PLA), poly(lactic-co-glycolic acid) (PLGA), and poly(lactic acid)-polyethyleneglycol (PLA-PEG) block copolymers), polyesters (e.g., polycaprolactone and polyhydroxyalkanoates such as poly-3-hydroxybutyrate (PHB) and poly-4-hydroxybutyrate (P4HB)), polyglycolides, polyanhydrides, poly(ester anhydrides), polyalkylene oxides (e.g., polyethylene glycols, polypropylene glycols, polybutylene glycols, and copolymers thereof), polyamines, polyurethanes, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly (amino acids), polyvinylpyrrolidone, polyethylene glycol, poly(amino acids), cellulosic polymers (e.g., cellulose and derivatives thereof, such as hydroxypropyl methyl cellulose, ethyl cellulose, methyl cellulose, sodium carboxymethyl cellulose (NaCMC), and polyhydroxycellulose), dextrans, gelatin, chitin, chitosan, alginates, hyaluronic acid, as well as copolymers (random copolymers as well as block copolymers), terpolymers and mixtures thereof. Examples of stimuli-responsive biocompatible polymers are also described, for example, in U.S. Patent Application Publication No. 2004/0138237, U.S. Patent Application Publication No. 2003/0180364, U.S. Patent Application Publication No. 2005/0143678, and U.S. Patent Application Publication No. 2004/0266983, each of which is hereby incorporated by reference in its entirety.

In some examples, the stimuli-responsive biocompatible polymer can comprise a polylactide, that is, a lactic acid-based polymer that can be based solely on lactic acid or can be a copolymer based on lactic acid, glycolic acid, and/or caprolactone, which may include small amounts of other comonomers. As used herein, the term "lactic acid" includes the isomers L-lactic acid, D-lactic acid, DL-lactic acid and lactide, while the term "glycolic acid" includes glycolide. Examples include polymers selected from the group consisting of polylactide polymers, commonly referred to as PLA, poly(lactide-co-glycolide)copolymers, commonly referred to as PLGA, and poly(caprolactone-co-lactic acid) (PCL-co-LA). In some examples, the polymer may have a monomer ratio of lactic acid/glycolic acid of from about 100:0 to about 15:85, preferably from about 75:25 to about 30:70, more preferably from about 60:40 to about 40:60, and an especially useful copolymer has a monomer ratio of lactic acid/glycolic acid of about 50:50.

The poly(caprolactone-co-lactic acid) (PCL-co-LA) polymer can have a comonomer ratio of caprolactone/lactic acid of from about 10:90 to about 90:10, from about 35:65 to about 65:35; or from about 25:75 to about 75:25. In certain embodiments, the lactic acid based polymer comprises a blend of about 0% to about 90% caprolactone, about 0% to about 100% lactic acid, and about 0% to about 60% glycolic acid.

The lactic acid-based polymer can have a number average molecular weight of from about 1,000 to about 120,000 (e.g., from about 5,000 to about 50,000, or from about 8,000 to about 30,000), as determined by gel permeation chromatography (GPC). As indicated in U.S. Pat. No. 5,242,910, the polymer can be prepared in accordance with the teachings of U.S. Pat. No. 4,443,340. Alternatively, the lactic acid-based polymer can be prepared directly from lactic acid or a mixture of lactic acid and glycolic acid (with or without a further comonomer) in accordance with the techniques set forth in U.S. Pat. No. 5,310,865. The contents of all of these patents are incorporated by reference. Suitable lactic acid-based polymers are available commercially. For instance, 50:50 lactic acid:glycolic acid copolymers having molecular weights of 8,000, 10,000, 30,000 and 100,000 are available from Boehringer Ingelheim (Petersburg, Va.), Medisorb Technologies International L.P. (Cincinatti, Ohio) and Birmingham Polymers, Inc. (Birmingham, Ala.) as described below.

Examples of polymers include, but are not limited to, Poly (D,L-lactide) Resomer® L104, PLA-L104, Poly (D,L-lactide-co-glycolide) 50:50 Resomer® RG502, Poly (D,L-lactide-co-glycolide) 50:50 Resomer® RG502H, Poly (D,L-lactide-co-glycolide) 50:50 Resomer® RG503, Poly (D,L-lactide-co-glycolide) 50:50 Resomer® RG506, Poly L-Lactide MW 2,000 (Resomer° L 206, Resomer® L 207, Resomer® L 209, Resomer® L 214); Poly D,L Lactide (Resomer® R 104, Resomer® R 202, Resomer® R 203, Resomer® R 206, Resomer® R 207, Resomer® R 208); Poly L-Lactide-co-D,L-lactide 90:10 (Resomer® LR 209); Poly glycolide (Resomer® G 205); Poly D,L-lactide-co-glycolide 50:50 (Resomer® RG 504 H, Resomer® RG 504, Resomer® RG 505); Poly D-L-lactide-co-glycolide 75:25 (Resomer® RG 752, Resomer® RG755, Resomer® RG 756); Poly D,L-lactide-co-glycolide 85:15 (Resomer® RG 858); Poly L-lactide-co-trimethylene carbonate 70:30 (Resomer® LT 706); Poly dioxanone (Resomer® X 210) (Boehringer Ingelheim Chemicals, Inc., Petersburg, Va.).

Additional examples include, but are not limited to, DL-lactide/glycolide 100:0 (MEDISORB® Polymer 100 DL High, MEDISORB® Polymer 100 DL Low); DL-lactide/glycolide 85/15 (MEDISORB® Polymer 8515 DL High, MEDISORB® Polymer 8515 DL Low); DL-lactide/glycolide 75/25 (MEDISORB® Polymer 7525 DL High, MEDISORB® Polymer 7525 DL Low); DL-lactide/glycolide 65/35 (MEDISORB® Polymer 6535 DL High, MEDISORB® Polymer 6535 DL Low); DL-lactide/glycolide 54/46 (MEDISORB® Polymer 5050 DL High, MEDISORB® Polymer 5050 DL Low); and DL-lactide/glycolide 54/46 (MEDISORB® Polymer 5050 DL 2A(3), MEDISORB® Polymer 5050 DL 3A(3), MEDISORB® Polymer 5050 DL 4A(3)) (Medisorb Technologies International L.P., Cincinati, Ohio); and Poly D,L-lactide-co-glycolide 50:50; Poly D,L-lactide-co-glycolide 65:35; Poly D,L-lactide-co-glycolide 75:25; Poly D,L-lactide-co-glycolide 85:15; Poly DL-lactide; Poly L-lactide; Poly glycolide; Poly ε-caprolactone; Poly DL-lactide-co-caprolactone 25:75; and Poly DL-lactide-co-caprolactone 75:25 (Birmingham Polymers, Inc., Birmingham, Ala.).

In certain embodiments, the stimuli-responsive biocompatible polymer can comprise an inverse thermosensitive polymer (i.e., a polymer that undergoes a transition from a liquid to a gel or solid in response to an increase in temperature). For example, the inverse thermosensitive polymer can exhibit a transition temperature of from 10° C. to 37° C. In some cases, the inverse thermosensitive polymer can be a liquid at 4° C., and undergoes a transition from a liquid to a gel or solid upon an increase in temperature from 4° C. to 37° C. In some cases, the inverse thermosensitive polymer can be a liquid at 23° C., and undergoes a transition from a liquid to a gel or solid upon an increase in temperature from 23° C. to 37° C.

A number of suitable inverse thermosensitive polymers are known in the art, and suitable for use in conjunction with the methods described herein. In some examples, the inverse thermosensitive polymer can comprise a block copolymer with inverse thermal gelation properties. The block copolymer can further comprise a biodegradable, biocompatible poly(alkylene oxide) block copolymer, such as a block copolymer of polyethylene oxide and polypropylene oxide.

Suitable inverse thermosensitive polymers include polyoxyethylene-polyoxypropylene (PEO-PPO) block copolymers. Two examples are PLURONIC® F127 and F108, which are PEO-PPO block copolymers with molecular weights of 12,600 and 14,600, respectively. Each of these compounds is available from BASF of Mount Olive, N.J. PLURONIC® acid F127 at 12-25% concentration in PBS is another example of a suitable material. In general, other biocompatible, biodegradable PEO-PPO block copolymers that exist as a gel at body temperature and a liquid at below body temperature may also be used.

Notably, PLURONIC® polymers have unique surfactant abilities and extremely low toxicity and immunogenic responses. These products have low acute oral and dermal toxicity and low potential for causing irritation or sensitization, and the general chronic and sub-chronic toxicity is low. In fact, PLURONIC® polymers are among a small number of surfactants that have been approved by the FDA for direct use in medical applications and as food additives (BASF (1990) PLURONIC® & TETRONIC® Surfactants, BASF Co., Mount Olive, N.J.).

The average molecular weights of the poloxamers range from about 1,000 to greater than 16,000 Daltons. Because the poloxamers are products of a sequential series of reactions, the molecular weights of the individual poloxamer molecules form a statistical distribution about the average molecular weight. In addition, commercially available poloxamers can contain substantial amounts of poly(oxyethylene) homopolymer and poly(oxyethylene)/poly(oxypropylene) diblock polymers. The relative amounts of these byproducts increase as the molecular weights of the component blocks of the poloxamer increase. Depending upon the manufacturer, these byproducts may constitute from about 15 to about 50% of the total mass of the polymer.

If desired, the inverse thermosensitive polymers may be purified using a process for the fractionation of water-soluble polymers, comprising the steps of dissolving a known amount of the polymer in water, adding a soluble extraction salt to the polymer solution, maintaining the solution at a constant optimal temperature for a period of time adequate for two distinct phases to appear, and separating physically the phases. Additionally, the phase containing the polymer fraction of the preferred molecular weight may be diluted to the original volume with water, extraction salt may be added to achieve the original concentration, and the separation process repeated as needed until a polymer having a narrower molecular weight distribution than the starting material and optimal physical characteristics can be recovered.

In certain embodiments, a purified poloxamer or poloxamine can have a polydispersity index from about 1.5 to about 1.0. In certain embodiments, a purified poloxamer or poloxamine can have a polydispersity index from about 1.2 to about 1.0. In certain embodiments, a purified poloxamer or poloxamine can have a polydispersity index from about 1.1 to about 1.0.

The aforementioned process consists of forming an aqueous two-phase system composed of the polymer and an appropriate salt in water. In such a system, a soluble salt can be added to a single-phase polymer-water system to induce phase separation to yield a high salt, low polymer bottom phase, and a low salt, high polymer upper phase. Lower molecular weight polymers partition preferentially into the high salt, low polymer phase. Polymers that can be fractionated using this process include polyethers, glycols such as poly(ethylene glycol) and poly(ethylene oxide)s, polyoxyalkylene block copolymers such as poloxamers, poloxamines, and polyoxypropylene/polyoxybutylene copolymers, and other polyols, such as polyvinyl alcohol. The average molecular weight of these polymers may range from about 800 to greater than 100,000 daltons. See U.S. Pat. No. 6,761,824. The aforementioned purification process inherently exploits the differences in size and polarity, and therefore solubility, among the poloxamer molecules, the poly(oxyethylene) homopolymer and the poly(oxyethylene)/poly(oxypropylene) diblock byproducts. The polar fraction of the poloxamer, which generally includes the lower molecular weight fraction and the byproducts, is removed allowing the higher molecular weight fraction of poloxamer to be recovered. The larger molecular weight poloxamer recovered by this method has physical characteristics substantially different from the starting material or commercially available poloxamer including a higher average molecular weight, lower polydispersity and a higher viscosity in aqueous solution.

Other purification methods may be used to achieve the desired outcome. For example, WO 92/16484 discloses the use of gel permeation chromatography to isolate a fraction of poloxamer 188 that exhibits beneficial biological effects, without causing potentially deleterious side effects. The copolymer thus obtained had a polydispersity index of 1.07 or less, and was substantially saturated. The potentially harmful side effects were shown to be associated with the low molecular weight, unsaturated portion of the polymer, while the medically beneficial effects resided in the uniform higher molecular weight material. Other similarly improved copolymers were obtained by purifying either the polyoxypropylene center block during synthesis of the copolymer, or the copolymer product itself (e.g., U.S. Pat. Nos. 5,523,492 and 5,696,298).

Further, a supercritical fluid extraction technique has been used to fractionate a polyoxyalkylene block copolymer as disclosed in U.S. Pat. No. 5,567,859. A purified fraction was obtained, which was composed of a fairly uniform polyoxyalkylene block copolymer having a polydispersity of less than 1.17. According to this method, the lower molecular weight fraction was removed in a stream of carbon dioxide maintained at a pressure of 2200 pounds per square inch (psi) and a temperature of 40° C.

Additionally, U.S. Pat. No. 5,800,711 discloses a process for the fractionation of polyoxyalkylene block copolymers by the batchwise removal of low molecular weight species using a salt extraction and liquid phase separation technique. Poloxamer 407 and poloxamer 188 were fractionated by this method. In each case, a copolymer fraction was obtained which had a higher average molecular weight and a lower polydispersity index as compared to the starting material. However, the changes in polydispersity index were modest and analysis by gel permeation chromatography indicated that some low-molecular-weight material remained. The viscosity of aqueous solutions of the fractionated polymers was significantly greater than the viscosity of the commercially available polymers at temperatures between 10° C. and 37° C., an important property for some medical and drug delivery applications. Nevertheless, some of the low molecular weight contaminants of these polymers are thought to cause deleterious side effects when used inside the body, making it especially important that they be removed in the fractionation process. As a consequence, polyoxyalkylene block copolymers fractionated by this process are not appropriate for all medical uses.

In some embodiments, the inverse thermosensitive polymers used comprise block polymers such as polyoxyethylene-polyoxypropylene (PEO-PPO) block polymers of the general structure A-B, (A-B)$_n$, A-B-A (e.g., a poloxamer or PLURONIC®), or (A-B-A)$_n$ with A being the PEO part and B being the PPO part and n being greater than 1. In other embodiments, the inverse thermosensitive polymers used comprise branched polymers of polyoxyethylene-polyoxypropylene (PEO-PPO) like tetra-functional poloxamines (e.g., a poloxamine or TETRONIC®). For example, the inverse thermosensitive polymer can comprise poloxamer 407, poloxamer 188, poloxamer 234, poloxamer 237, poloxamer 338, poloxamine 1107, poloxamine 1307, or a combination thereof.

In some embodiments, the inverse thermosensitive polymer can comprise poloxamer 407, poloxamer 188, or a combination thereof.

In certain embodiments, the inverse thermosensitive polymer can comprise (i) from 20% to 40% by weight of a first inverse thermosensitive polymer defined by Formula I below

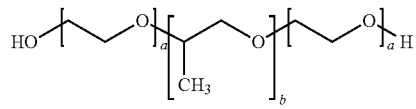

Formula I wherein a is an integer from 90 to 110 and b is an integer from 50 to 60, wherein the first inverse thermosensitive polymer has a molecular weight of from 9,500 Da to 15,000 Da, and wherein the first inverse thermosensitive polymer has a polyoxyethylene content of from 70% to 75%; and (ii) from 5% to 50% by weight of a second inverse thermosensitive polymer defined by Formula I below

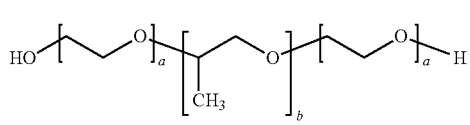

Formula I wherein a is an integer from 70 to 90 and b is an integer from 20 to 35, wherein the first inverse thermosensitive polymer has a molecular weight of from 7,500 Da to 10,000 Da, and wherein the first inverse thermosensitive polymer has a polyoxyethylene content of from 78% to 85%.

In another example, the stimuli-responsive biocompatible polymer can comprise a PCLA-PEG-PCLA tri-block copolymer, such as those marketed under the tradename INGELL® by Innocore Pharmaceuticals.

The stimuli-responsive biocompatible polymer can be present in the liquid composition in an amount ranging from 20% to 95% by weight (from 20% to about 85% by weight).

In some embodiments, the liquid composition can further comprise a solvent (e.g., water, saline, a buffer solution, DMSO, ethanol, methanol, glutaraldehyde, or combinations thereof).

Crosslinkable Biomaterials

In some embodiments, liquid compositions can include a crosslinkable biomaterial. Suitable crosslinkable biomaterials can include a variety of natural and/or synthetic materials. In certain embodiments, the polymeric matrix can be a hydrogel. Hydrogels are water-swellable materials formed from oligomeric or polymeric molecules which are crosslinked to form a three-dimensional network. Hydrogels can be designed to form in situ (for example, from injectable precursors which crosslink in vivo). As gels, these materials can exhibit properties characteristic of both liquids (e.g., their shape can be resilient and deformable) and solids (e.g., their shape can be discrete enough to maintain three dimensions on a two-dimensional surface).

The crosslinkable biomaterial can be designed to rapidly cure in situ upon injection. In some embodiments, the crosslinkable biomaterial has a cure time of less than about 20 minutes (e.g., less than about 15 minutes, less than about 10 minutes, less than about 5 minutes, less than about 3 minutes, or less than about 1 minute).

The crosslinkable biomaterial injected can have a low viscosity relative to the resulting polymeric matrix. This can allow the crosslinkable biomaterial to be readily injected, for example, via a hand-powered delivery device such as a syringe. This can provide a physician with a large degree of control over the flow rate of the crosslinkable biomaterial during injection, and allow the flow to be altered or stopped, as required, during the course of injection. The relatively low viscosity of the crosslinkable biomaterial relative to the polymeric matrix also can allow the crosslinkable biomaterial to conform to the anatomy of the treatment site.

For example, in some embodiments, the crosslinkable biomaterial has a viscosity of about 1,000 cP or less (e.g., about 900 cP or less, about 800 cP or less, about 750 cP or less, about 700 cP or less, about 600 cP or less, about 500 cP or less, about 400 cP or less, about 300 cP or less, about 250 cP or less, about 200 cP or less, about 150 cP or less, about 100 cP or less, or. about 50 cP or less) at room temperature. In certain cases, the crosslinkable biomaterial has a viscosity of at least 1 cP (e.g., at least 2 cP, at least 2.5 cP, at least 5 cP, or at least 10 cP) at room temperature. The crosslinkable biomaterial can have a viscosity ranging from any of the minimum values described above to any of the maximum values described above.

In some embodiments, the crosslinkable biomaterial comprises a multicomponent (e.g., bicomponent) composition which crosslinks in situ to form the polymeric matrix. For example, the crosslinkable biomaterial can comprise a first precursor molecule and a second precursor molecule. "Precursor molecule", as used herein, generally refers to a molecule present in the crosslinkable biomaterial which interacts with (e.g., crosslinks with) other precursor molecules of the same or different chemical composition in the crosslinkable biomaterial to form a polymeric matrix. Precursor molecules can include monomers, oligomers and polymers which can be crosslinked covalently and/or non-covalently.

The multiple components of the composition (e.g., the first precursor molecule and the second precursor molecule) can be combined prior to injection, can be present in two or more separate solutions which are combined during the injection (e.g., by mixing within a device such as a used to inject the material), or can be present in two or more separate solutions which are individually injected into the treatment site.

In some embodiments, the crosslinkable biomaterial comprises a first precursor molecule present in a first solution and a second precursor molecule present in a second solution. In one embodiment, the two solutions are combined during the course of injection (e.g., by mixing within a delivery device used to inject the material). In another embodiment, the two solutions are individually injected into the treatment site, and combine in situ. In these cases, the two solutions can be injected simultaneously or sequentially. Depending on the mechanism of crosslinking, an accelerator (e.g., a pH modifying agent or radical initiator) can be added and/or an external stimulus (e.g., UV irradiation) can be applied to ensure uniform and rapid curing of the crosslinkable biomaterial to form a polymeric matrix. In cases where an accelerator is added, the accelerator can be incorporated into one or more of the solutions containing a precursor molecule prior to injection. The accelerator can also be present in a solution which does not contain a precursor molecule. This accelerator solution can then be injected simultaneously or sequentially with one or more solutions containing one or more precursor compounds to initiate formation of the polymeric matrix.

Suitable precursor molecules can be selected in view of the desired properties of the crosslinkable biomaterial and resultant polymeric matrix. In some cases, the crosslinkable biomaterial comprises one or more oligomeric or polymeric precursor molecules. For example, precursor molecules can include, but are not limited to, polyether derivatives, such as poly(alkylene oxide)s or derivatives thereof, polysaccharides, peptides, and polypeptides, poly(vinyl pyrrolidinone) ("PVP"), poly(amino acids), and copolymers thereof.

The precursor molecules can further comprise one or more reactive groups. Reactive groups are chemical moieties in a precursor molecule which are reactive with a moiety (such as a reactive group) present in another precursor molecule to form one or more covalent and/or non-covalent bonds. Examples of suitable reactive groups include, but are not limited to, active esters, active carbonates, aldehydes, isocyanates, isothiocyanates, epoxides, alcohols, amines, thiols, maleimides, groups containing one or more unsaturaturated C—C bonds (e.g., alkynes, vinyl groups, vinylsulfones, acryl groups, methacryl groups, etc.), azides, hydrazides, dithiopyridines, N-succinimidyl, and iodoacetamides. Suitable reactive groups can be incorporated in precursor molecules to provide for crosslinking of the precursor molecules.

In some embodiments, one or more of the precursor molecules comprises a poly(alkylene oxide)-based oligomer or polymer. Poly(alkylene oxide)-based oligomer and polymers are known in the art, and include polyethylene glycol ("PEG"), polypropylene oxide ("PPO"), polyethylene oxide-co-polypropylene oxide ("PEO-PPO"), co-polyethylene oxide block or random copolymers, poloxamers, meroxapols, poloxamines, and polyvinyl alcohol ("PVA"). Block copolymers or homopolymers (when A=B) may be linear (AB, ABA, ABABA or ABCBA type), star ($A_nB$ or $BA_nC$, where B is at least n-valent, and n is an integer of from 3 to 6) or branched (multiple A's depending from one B). In certain embodiments, the poly(alkylene oxide)-based oligomer or polymer comprises PEG, a PEO-PPO block copolymer, or combinations thereof.

In some embodiments, one or more of the precursor molecules is defined by Formula I or Formula II

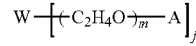

Formula I

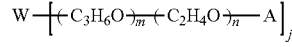

Formula II wherein
W is a branch point;
A is a reactive group (e.g., a nucleophilic group or a conjugated unsaturated group);
m and n are integers of from 1 to 500 (e.g., an integers of from 1 to 200); and
j is an integer greater than 2 (e.g., an integer of from 2 to 8).

In some embodiments, one or more of the precursor molecules comprises a biomacromolecule. The biomacromolecule can be, for example, a protein (e.g., collagen) or a polysaccharide. Examples of suitable polysaccharides include cellulose and derivatives thereof, dextran and derivatives thereof, hyaluronic acid and derivatives thereof, chitosan and derivatives thereof, alginates and derivatives thereof, and starch or derivatives thereof. Polysaccharides can derivatized by methods known in art. For example, the polysaccharide backbone can be modified to influence polysaccharide solubility, hydrophobicity/hydrophilicity, and the properties of the resultant polymeric matrix formed from the polysaccharide (e.g., matrix degradation time). In certain embodiments, one or more of the precursor molecules comprises a biomacromolecule (e.g., a polysaccharide) which is substituted by two or more (e.g., from about 2 to about 100, from about 2 to about 25, or from about 2 to about 15) reactive groups (e.g., a nucleophilic group or a conjugated unsaturated group).

In some cases, the crosslinkable biomaterial can comprise a first precursor molecule which comprises an oligomer or polymer having one or more first reactive groups, each first reactive group comprising one or more pi bonds, and a second precursor molecule comprises an oligomer or polymer having one or more second reactive groups, each second reactive group comprising one or more pi bonds. The first reactive group can be reactive (e.g., via a Click chemistry reaction) with the second reactive group, so as to form a covalent bond between the first precursor molecule and the second precursor molecule. For example, the first reactive group and the second reactive group undergo a cycloaddition reaction, such as a [3+2] cycloaddition (e.g., a Huisgen-type 1,3-dipolar cycloaddition between an alkyne and an azide) or a Diels-Alder reaction.

In some cases, the crosslinkable biomaterial can comprise a first precursor molecule which comprises an oligomer or polymer having one or more nucleophilic groups (e.g. amino groups, thiol groups hydroxy groups, or combinations thereof), and a second precursor molecule which comprises an oligomer or polymer having one or more conjugated unsaturated groups (e.g., vinyl sulfone groups, acryl groups, or combinations thereof). In such cases, the first precursor molecule and the second precursor molecule can react via a Michael-type addition reaction. Suitable conjugated unsaturated groups are known in the art, and include those moieties described in, for example, U.S. Patent Application Publication No. 2008/0253987 to Rehor, et al., which is incorporated herein by reference in its entirety.

In certain embodiments, the crosslinkable biomaterial can comprise a first precursor molecule and a second precursor molecule. The first precursor molecule comprises a poly(alkylene oxide)-based oligomer or polymer having x nucleophilic groups, wherein x is an integer greater than or equal to 2 (e.g., an integer of from 2 to 8, or an integer of from 2 to 6). The poly(alkylene oxide)-based polymer can comprise, for example, poly(ethylene glycol). The nucleophilic groups can be selected from the group consisting of sulfhydryl groups and amino groups. The first precursor molecule can have a molecular weight of from about 1 kDa to about 10 kDa (e.g., from about 1 kDa to about 5 kDa). In some embodiments, the first precursor molecule comprises pentaerythritol poly(ethylene glycol)ether tetrasulfhydryl.

The second precursor molecule can comprises a biomacromolecule having y conjugated unsaturated groups, wherein y is an integer greater than or equal to 2 (e.g., an integer of from 2 to 100, or an integer of from 2 to 25). The biomacromolecule can comprise a polysaccharide, such as dextran, hyaluronic acid, chitosan, alginate, or derivatives thereof. The conjugated unsaturated groups can be selected from the group consisting of vinyl sulfone groups and acryl groups. The second precursor molecule can have a molecular weight of from about 2 kDa to about 250 kDa (e.g., from about 5 kDa to about 50 kDa). In some embodiments, the second precursor molecule comprises dextran vinyl sulfone.

In some embodiments, the in situ crosslinking of the precursor molecules takes place under basic conditions. In these embodiments, the crosslinkable biomaterial can further include a base to activate the crosslinking of the precursor molecules. A variety of bases comply with the requirements of catalyzing, for example, Michael addition reactions under physiological conditions without being detrimental to the patient's body. Suitable bases include, but are not limited to, tertiary alkyl-amines, such as tributylamine, triethylamine, ethyldiisopropylamine, or N,N-dimethylbutylamine. For a given composition (and mainly dependent on the type of precursor molecules), the gelation time can be dependent on the type of base and of the pH of the solution. Thus, the gelation time of the composition can be controlled and adjusted to the desired application by varying the pH of the basic solution.

In some embodiments, the base, as the activator of the covalent crosslinking reaction, is selected from aqueous buffer solutions which have their pH and pK value in the same range. The pK range can be between 9 and 13. Suitable buffers include, but are not limited to, sodium carbonate, sodium borate and glycine. In one embodiment, the base is sodium carbonate.

The crosslinkable biomaterial can further contain organic and/or inorganic additives, such as thixotropic agents, stabilizers for stabilization of the precursor molecules in order to avoid premature crosslinking, and/or fillers which can result in an increase or improvement in the mechanical properties (e.g., cohesive strength and/or elastic modulus) of the resultant biocompatible matrix. Examples of stabilizing agents include radical scavengers, such as butylated hydroxytoluene or dithiothreitol.

In some embodiments, the liquid composition can further comprise a solvent (e.g., water, saline, a buffer solution, DMSO, ethanol, methanol, glutaraldehyde, or combinations thereof).

Heat-Activated Biocompatible Polymers

In some embodiments, the liquid compositions can include a heat-activated biocompatible polymer. The heat-activated biocompatible polymer can comprise any suitable biocompatible polymer(s) that undergo an irreversible transition from a liquid to a solid or gel at a temperature greater than physiological temperature (e.g., a temperature of from 40° C. to 70° C.). In some embodiments, the heat-activated biocompatible polymer can comprise any biocompatible polymeric material which undergoes a crosslinking reaction at a temperature greater than physiological temperature (e.g., a temperature of from 40° C. to 70° C.).

For example, the heat-activated biocompatible polymer can comprise a crosslinkable polymer and a thermally activated crosslinker. Examples of crosslinkable polymers include, but are not limited to, polylactides (e.g., poly(lactic acid) (PLA), poly(lactic-co-glycolic acid) (PLGA), and poly(lactic acid)-polyethyleneglycol (PLA-PEG) block copolymers), polyesters (e.g., polycaprolactone and polyhydroxyalkanoates such as poly-3-hydroxybutyrate (PHB) and poly-4-hydroxybutyrate (P4HB)), polyglycolides, polyanhydrides, poly(ester anhydrides), polyalkylene oxides (e.g., polyethylene glycols, polypropylene glycols, polybutylene glycols, and copolymers thereof), polyamines, polyurethanes, polyesteramides, polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, poly(amino acids), cellulosic polymers (e.g., cellulose and derivatives thereof, such as hydroxypropyl methyl cellulose, ethyl cellulose, methyl cellulose, sodium carboxymethyl cellulose (NaCMC), and polyhydroxycellulose), dextrans, gelatin, chitin, chitosan, alginates, hyaluronic acid, as well as copolymers (random copolymers as well as block copolymers), terpolymers and mixtures thereof.

The thermally activated crosslinker can comprise a crosslinking agent for the crosslinkable polymer encapsulated in a lipid vesicle. The lipid vesicle can be formulated to degrade at a temperature of from 40° C. to 70° C., allowing the crosslinking agent to be released locally to crosslink the crosslinkable polymer when the heat-activated biocompatible polymer is heated.

Heat-activated systems of this type are known in the art, and described, for example, in U.S. Patent Application Publication No. 2008/0247984, which is hereby incorporated by reference in its entirety.

In certain embodiments, the liquid composition can exhibit a viscosity of less than 1000 cP at 4° C. (e.g., to facilitate injectability). For example, in some embodiments, the liquid composition can exhibit a viscosity of less than 500 cP, less than 250 cP, or less than 100 cP at 4° C. Upon exposure to heat generated by the RF ablation probe (e.g., a temperature of from 40° C. to 70° C.), the heat-activated biocompatible polymer forms a polymeric matrix that exhibits a viscosity of at least 25,000 cP at 37° C. (e.g., a viscosity of from 25,000 cP to 100,000 cP at 37° C.).

In another example, the heat-activated biocompatible polymer can comprise a bi-component system. The two part systems may be added either both at the same time or in succession. One component can comprise a polymer or monomer solution that has low viscosity and will not interact with itself. The second component can include a carrier and a chemically reactive ingredient. The carrier can be formulated out of thermo sensitive linkages or particles that have a desired critical solution temperature. The carrier can act in such a way that when exposed to temperatures below 50° C., the carrier remains intact and migrates away from the ablation site; however, at temperatures between 50-90° C., the carrier decomposes or transitions in a way that releases its cargo at or near the temperature signal of the lesion.

When the bi-component system is administered there is no chemical reaction at physiological temperatures and remains inert. If there is not a localized increase in temperature, the two chemical parts of the device will not interact to form a viscous gel, physical barrier, thus will be secreted out of the patient. However, at elevated temperatures above 50° C., the cargo of the carrier component will release the chemical reagent that interacts with the other component of the device that triggers the formation of a the gel by a chemical or covalent cross linking. The nature of the carrier is to facilitate the cross-linking gelling event. The composition may vary depending on the formulation used: redox/radical initiator and stabilizer, ionic salt solutions, nucleophilic proteins or polymers, and electrophilic proteins or polymers. The carrier can be comprised of a material that destabilizes at the target temperature of the lesion. For example, the carrier can comprise a single or blend of polymers, which include: poly(N-isopropylacrylamide), poly(ethylene glycol) (pHPMAmDL-b-PEG), and poly(hydroxypropyl methacrylamide-lactate) that are processed as particles or viscous gels.

The heat-activated biocompatible polymer can be present in the liquid composition in an amount ranging from 20% to 95% by weight (from 20% to about 85% by weight).

In some embodiments, the liquid composition can further comprise a solvent (e.g., water, saline, a buffer solution, DMSO, ethanol, methanol, glutaraldehyde, or combinations thereof).

Biocompatible Materials and Particles

In some embodiments, the liquid compositions can include a biocompatible material. The biocompatible material can comprise any suitable biocompatible material(s) that undergo an irreversible transition from a liquid to a solid or gel upon injection. In some embodiments, the material can undergo a crosslinking reaction upon injection. In other embodiments, the material can swell and become insoluble upon injection.

Examples of suitable materials include, for example, polymer particles which comprise a complex of crosslinked sodium polyacrylate with a copolymer of polyvinyl alcohol-polyvinyl acetate (e.g., a Vantris-type formulation), polydimethylsiloxane (e.g., such as compositions sold under the tradename MARCOPLASTIQUE®), injectable calcium phosphate cements, and crosslinkable polyurethanes (e.g., a lysine-derived polyurethane).

In some embodiments, the biocompatible material can comprise polymeric, water-insoluble, non-biodegradable, anionic particles having irregular shapes. The polymeric particles can be present in the composition in an amount ranging from 0.5% to less than 5% by weight, relative to the total weight of the injectable composition. The polymeric particles comprise particles having a size ranging from 150 to 800 microns. The polymeric particles can comprise, for example, particles of a complex of crosslinked sodium polyacrylate polymer with a copolymer of polyvinyl alcohol-polyvinyl acetate; pegylated forms of the complex of crosslinked sodium polyacrylate polymer with a copolymer of polyvinyl alcohol-polyvinyl acetate; combinations thereof; and mixtures thereof with particles of pegylated forms of crosslinked sodium polyacrylate polymer. The complex of crosslinked sodium polyacrylate polymer with a copolymer of polyvinyl alcohol-polyvinyl acetate can have a molecular weight ranging from 7000 to 13000 kDa. The copolymer polyvinyl alcohol-polyvinyl acetate can have a molecular weight ranging from 25 to 100 kDa. The composition can further include a biocompatible carrier with lubricating properties, chosen from glycerol in a concentration ranging from 15% to 60% in distilled water or isotonic saline solution. When injected, the composition can be in the form of swelled hydrogel particles having a diameter ranging from 0.6 to 3.0 mm. Such compositions are described, for example, in U.S. Pat. No. 9,017,709, which is hereby incorporated by reference in its entirety.

Other suitable materials include polydimethylsiloxane (e.g., such as compositions sold under the tradename MARCOPLASTIQUE® and those described in U.S. Pat. No. 5,792,478, which is hereby incorporated by reference in its entirety), injectable calcium phosphate cements, and crosslinkable polyurethanes (e.g., a lysine-derived polyurethane).

In certain embodiments, the liquid composition can exhibit a viscosity of less than 1000 cP at 4° C. (e.g., to facilitate injectability). For example, in some embodiments, the liquid composition can exhibit a viscosity of less than 500 cP, less than 250 cP, or less than 100 cP at 4° C. Upon injection, the biocompatible material forms a matrix that exhibits a viscosity of at least 25,000 cP at 37° C. (e.g., a viscosity of from 25,000 cP to 100,000 cP at 37° C.).

In some cases, the biocompatible material can be present in the liquid composition in an amount ranging from 20% to 95% by weight (from 20% to about 85% by weight).

These liquid compositions can further comprise a population of energy-absorbing particles. Examples of suitable energy-absorbing particles include, for example, nanoshells, nanorods, carbon nanotubes, fullerenes, paramagnetic particles, metallic nanoparticles, and other absorbers of electromagnetic energy or absorbers of acoustic energy. Example energy sources, and corresponding energy-absorbing particles are known in the art, and described for example in U.S. Patent Application Publication Nos. 2011/0052672 and 2011/0034916, each of which is hereby incorporated by reference in its entirety.

In some embodiments, the liquid composition can further comprise a solvent (e.g., water, saline, a buffer solution, DMSO, ethanol, methanol, glutaraldehyde, or combinations thereof).

Active Agents

In some embodiments, the liquid composition can further comprise an active agent. The active agent can be a therapeutic agent, a prophylactic agent, a diagnostic agent, or a combination thereof. For example, the active agent can comprise an anti-nerve growth factor, an anti-inflammatory agent, an analgesic, a contrast agent, a biomarker for monitoring clearance of the polymeric matrix, an NGF/TrkA pathway inhibitor, a substance P inhibitor, a CGRO inhibitor, extracellular matrix molecule proteins, or a combination thereof.

Examples of anti-nerve growth factors include antibodies against nerve growth factor (ngf), such as those described in U.S. Pat. Nos. 7,655,231, 7,252,822, U.S. Patent Application Publication No. 2010/0278839, U.S. Pat. No. 6,919,426, U.S. Patent Application Publication No. 2011/0256135, and U.S. Patent Application Publication No. 2014/0170136, each of which is hereby incorporated herein by reference in its entirety.

Examples of anti-inflammatory agents include both steroidal and non-steroidal anti-inflammatory agents. Non-limiting examples of steroidal anti-inflammatory agents include corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chloroprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof. Non-limiting examples of non-steroidal anti-inflammatory agents include oxicams (e.g., piroxicam, isoxicam, tenoxicam, sudoxicam, CP-14,304); salicylates (e.g., aspirin, disalcid, benorylate, trilisate, safapryn, solprin, diflunisal, fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, ketorolac); fenamates (e.g., mefenamic, meclofenamic, flufenamic, niflumic, tolfenamic acids); propionic acid derivatives (e.g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, tiaprofenic); pyrazoles (e.g., phenylbutazone, oxyphenbutazone, feprazone, azapropazone, trimethazone); and combinations thereof as well as any dermatologically acceptable salts or esters of thereof. COX-2 inhibitors are also suitable for use herein, and include, but are not limited to, AZD 3582 (ASTRAZENECA and NicOx), Celecoxib (PHARMACIA Corp.) (4-[5-(4-methylphenyl)-3-(trifluoromethyl)-1H-pyrazol-1-yl]benzenesulfonamide), Meloxicam (BOEHRINGER INGELHEIM Pharmaceuticals) (4-hydroxy-2-methyl-N-(5-methyl-2-thiazolyl)-2H-1,2GW-406381 (GLAXOSMITHKLINE), Etoricoxib (MERCK & Co.), Rofecoxib (MERCK & Co.) (4-[4-(methylsulfonyl) phenyl]-3-phenyl-2(5H)-furanone), Lumiracoxib (NOVARTIS Pharma AG), Valdecoxib (PHARMACIA Corp.) (4-(5-methyl-3-phenyl-4-isox-azolyl) benzenesulfonamide), and Etodolac (WYETH Ayerst Laboratories) ((.+−.) 1,8-diethyl-1,3,4,9-tetrahydropyrano-[3,4-b]acid).

Examples of analgesic agents include, but are not limited to: capsaicin, indomethacin, centrally acting analgesics such as clonidine and tramadol, and narcotic analgesics or narcotic "painkillers", examples of which include, by way of illustration, alfentanil, buprenorphine, butorphanol, codeine, enkephalin, fentanyl, hydrocodone, hydromorphone, levorphanol, meperidine, methadone, morphine, nicomorphine, opium, oxycodone, oxymorphone, pentazocine, propoxyphene, and sufentanil.

In some examples, the liquid composition can further comprise a contrast agent. Upon injection, the contrast agent can be retained (e.g., dissolved or dispersed in) the polymeric matrix. In these embodiments, methods can further comprise imaging the polymeric matrix (e.g., to confirm placement of the polymeric matrix at the treatment site, to monitor clearance of the polymeric matrix from the treatment site, or a combination thereof). Examples of suitable contrast agents include ultrasound contrast agents, x-ray/radiocontrast agents (e.g., iodo-octanes, halocarbons, renografin, metrizamide, iohexol, iopamidol, iothalamate sodium, iodomide sodium, meglumine, and metal and metal oxide particles), magnetic contrast agents (e.g., fluorocarbons, lipid soluble paramagnetic compounds, GdDTPA, aqueous paramagnetic compounds, and the like).

Ablation Probes

The ablation probe can comprise any suitable ablation probe known in the art for use in neural ablation procedures. For example, in some cases, the ablation probe can comprise a radiofrequency (RF) ablation probe, and the ablating step comprises applying energy using the RF probe to ablate the nerve. In certain cases, the radiofrequency (RF) ablation probe is actively or passively cooled. In other examples (e.g., wherein the liquid composition does not comprise a heat-activated biocompatible polymer), the ablation probe can comprise a cryogenic ablation probe, and the ablating step comprises cooling the nerve using the cryogenic ablation probe.

Example ablation probes and systems are described, for example, in U.S. Pat. Nos. 8,882,755, 7,306,596, 8,187,268, 9,486,275, 7,163,536, 8,361,063, 7,076,399, 7,533,002, 7,596,469, 9,265,559, and 7,258,688, each of which is hereby incorporated herein by reference in its entirety.

Other examples of ablation probes include, for example, those described in U.S. Pat. Nos. 9,186,197, 8,361,067, and 6,721,603, each of which is hereby incorporated herein by reference in its entirety.

Introducers

The introducer cannula can comprise any suitable cannula sized and dimensioned to provide percutaneous access to the treatment site. Generally, the introducer comprises a central channel sized and configured to receive the ablation probe and the delivery tip of a syringe therethrough. If desired for delivery of a particular liquid composition, the introducer cannula is actively or passively cooled during the ablation step, during the injection step, or any combination thereof.

Syringes

The liquid composition can be injected using a syringe or other suitable implement that facilitates delivery of the liquid composition to the treatment site. Any suitable syringe may be used.

In some embodiments, the syringe can comprise a barrel defining a volume for containing from 1 mL to 10 mL (e.g., from 1 mL to 5 mL) of a liquid composition, a distal end of the barrel including a delivery tip; and a plunger sized and configured to move within the volume of the barrel to convey the liquid composition through the delivery tip.

If desired, the syringe can further include a cooling mechanism (e.g., an insulating sheath, or a cooling pack) for regulating a temperature of the liquid composition within the volume of the barrel. Examples of suitable syringes are described, for example, in U.S. Provisional Application No. 62/745,652, entitled "SYSTEMS AND METHODS FOR DELIVERING A POLYMERIC MATERIAL TO A TREATMENT SITE DURING A RF ABLATION PROCEDURE", filed on Oct. 15, 2018, and U.S. Ser. No. 16/653,135, entitled "SYSTEMS AND METHODS FOR DELIVERING A POLYMERIC MATERIAL TO A TREATMENT SITE DURING A RF ABLATION PROCEDURE", filed on Oct. 15, 2019, both of which is hereby incorporated by reference in its entirety. In some embodiments, a thermally controlled syringe of this type can be used to store and deliver a liquid composition comprising an inverse thermosensitive polymer.

In some embodiments, the liquid composition can comprise a bicomponent crosslinkable biomaterial comprising a first precursor solution and a second precursor solution. In these embodiments, the syringe can comprise a dual barrel syringe comprising a first barrel defining a volume for containing the first precursor solution, a distal end of the first barrel fluidly connected to a delivery tip; a second barrel defining a volume for containing the second precursor solution, a distal end of the second barrel fluidly connected to a delivery tip; and a plunger sized and configured to move within the volume of the first barrel and the volume of the second barrel to convey the first precursor solution and the second precursor solution through the delivery tip. Examples of suitable dual barrel syringes are known in the art. See, for example, U.S. Pat. No. 5,116,315, which is hereby incorporated by reference in its entirety.

Systems

Also provided herein are systems for use in conjunction with the methods described herein.

For example, provided herein are systems for neural ablation that comprise (i) a liquid composition comprising a stimuli-responsive biocompatible polymer; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough.

As discussed above, the ablation probe can comprise any suitable ablation probe known in the art for use in neural ablation procedures. For example, in some cases, the ablation probe can comprise a radiofrequency (RF) ablation probe (e.g., a cooled RF probe). In other examples, the ablation probe can comprise a cryogenic ablation probe.

Likewise, the introducer cannula can comprise any suitable cannula sized and dimensioned to provide percutaneous access to the treatment site. Generally, the introducer comprises a central channel sized and configured to receive the ablation probe and the delivery tip of the syringe therethrough.

Any suitable syringe may be used. In some embodiments, the syringe can comprise a barrel defining a volume for containing from 1 mL to 10 mL (e.g., from 1 mL to 5 mL) of a liquid composition, a distal end of the barrel including a delivery tip; and a plunger sized and configured to move within the volume of the barrel to convey the liquid composition through the delivery tip.

The syringe can further include a cooling mechanism (e.g., an insulating sheath, or a cooling pack) for regulating a temperature of the liquid composition within the volume of the barrel. The liquid composition can be any suitable composition described herein.

Also provided are systems for neural ablation that comprise (i) a liquid composition comprising a stimuli-responsive biocompatible polymer; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough.

In some embodiments, the crosslinkable biomaterial can be a bicomponent crosslinkable biomaterial comprising a first precursor solution and a second precursor solution. These embodiments, the system can include a dual barrel syringe for delivery of the first precursor solution and a second precursor solution. Accordingly, also provided are systems for neural ablation comprising: (i) a bicomponent crosslinkable biomaterial comprising a first precursor solution and a second precursor solution; (ii) a dual barrel syringe comprising a first barrel defining a volume for containing the first precursor solution, a distal end of the first barrel fluidly connected to a delivery tip; a second barrel defining a volume for containing the second precursor solution, a distal end of the second barrel fluidly connected to a delivery tip; and a plunger sized and configured to move within the volume of the first barrel and the volume of the second barrel to convey the first precursor solution and the second precursor solution through the delivery tip; (iii) an ablation probe; and (iv) an introducer cannula comprising a central channel sized and configured to receive the ablation probe and the delivery tip therethrough.

As discussed above, the ablation probe can comprise any suitable ablation probe known in the art for use in neural ablation procedures. For example, in some cases, the ablation probe can comprise a radiofrequency (RF) ablation probe (e.g., a cooled RF probe). In other examples, the ablation probe can comprise a cryogenic ablation probe.

Likewise, the introducer cannula can comprise any suitable cannula sized and dimensioned to provide percutaneous access to the treatment site. Generally, the introducer comprises a central channel sized and configured to receive the ablation probe and the delivery tip of the syringe therethrough.

Any suitable syringe may be used. In some embodiments, the syringe can comprise a barrel defining a volume for containing from 1 mL to 10 mL (e.g., from 1 mL to 5 mL) of a liquid composition, a distal end of the barrel including a delivery tip; and a plunger sized and configured to move within the volume of the barrel to convey the liquid composition through the delivery tip.

In some embodiments, the crosslinkable biomaterial can be a bicomponent crosslinkable biomaterial comprising a first precursor solution and a second precursor solution. In these embodiments, the syringe can comprise a dual barrel syringe comprising a first barrel defining a volume for containing the first precursor solution, a distal end of the first barrel fluidly connected to a delivery tip; a second barrel defining a volume for containing the second precursor solution, a distal end of the second barrel fluidly connected to a delivery tip; and a plunger sized and configured to move within the volume of the first barrel and the volume of the second barrel to convey the first precursor solution and the second precursor solution through the delivery tip Also provided herein are systems for neural ablation that comprise (i) a liquid composition comprising a heat-activated biocompatible polymer; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an RF ablation probe; and (iv) an introducer cannula comprising a central channel sized and configured to receive the ablation probe and the delivery tip therethrough.

As discussed above, the ablation probe can comprise any suitable RF ablation probe known in the art for use in neural ablation procedures. For example, in some cases, the ablation probe can comprise a cooled RF probe.

Likewise, the introducer cannula can comprise any suitable cannula sized and dimensioned to provide percutaneous access to the treatment site. Generally, the introducer comprises a central channel sized and configured to receive the ablation probe and the delivery tip of the syringe therethrough.

Any suitable syringe may be used. In some embodiments, the syringe can comprise a barrel defining a volume for containing from 1 mL to 10 mL (e.g., from 1 mL to 5 mL) of a liquid composition, a distal end of the barrel including a delivery tip; and a plunger sized and configured to move within the volume of the barrel to convey the liquid composition through the delivery tip.

The syringe can further include a cooling mechanism (e.g., an insulating sheath, or a cooling pack) for regulating a temperature of the liquid composition within the volume of the barrel. The liquid composition can be any suitable composition described herein.

Also provided are systems for neural ablation that comprise (i) a liquid composition comprising a non-erodible biocompatible material and a population of energy-absorbing particles; (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough.

As discussed above, the ablation probe can comprise any suitable ablation probe known in the art for use in neural ablation procedures. For example, in some cases, the ablation probe can comprise a radiofrequency (RF) ablation probe (e.g., a cooled RF probe). In other examples, the ablation probe can comprise a cryogenic ablation probe.

Likewise, the introducer cannula can comprise any suitable cannula sized and dimensioned to provide percutaneous access to the treatment site. Generally, the introducer comprises a central channel sized and configured to receive the ablation probe and the delivery tip of the syringe therethrough.

Any suitable syringe may be used. In some embodiments, the syringe can comprise a barrel defining a volume for containing from 1 mL to 10 mL (e.g., from 1 mL to 5 mL) of a liquid composition, a distal end of the barrel including a delivery tip; and a plunger sized and configured to move within the volume of the barrel to convey the liquid composition through the delivery tip.

The syringe can further include a cooling mechanism (e.g., an insulating sheath, or a cooling pack) for regulating a temperature of the liquid composition within the volume of the barrel. The liquid composition can be any suitable composition described herein.

Kits

Also described are kits for performing a neural ablation procedure described herein. The kits can comprise the components of a system described herein (e.g., (i) a liquid composition described herein (e.g., a liquid composition comprising a stimuli-responsive biocompatible polymer, a liquid composition comprising a crosslinkable biomaterial, a liquid composition comprising a non-erodible biocompatible material and a population of energy-absorbing particles, or a liquid composition comprising a heat-activated biocompatible polymer); (ii) a syringe comprising a barrel defining a volume for containing the liquid composition, a distal end of the barrel including a delivery tip; and a plunger sized and configured to move within the volume of the barrel to convey the liquid composition through the delivery tip; (iii) an ablation probe; and (iv) an introducer cannula comprising a central channel sized and configured to receive the ablation probe and the delivery tip therethrough) enclosed within sterile packaging.

In some cases, the liquid composition can be loaded within the syringe. In other embodiments, the liquid composition can be packaged in a separate vial or container. In these embodiments, the liquid composition can be loaded within the syringe prior to use.

In some embodiments, the kit can further include a cooling mechanism (e.g., a physically activated cooling pack) for cooling the liquid composition prior to use.

In certain embodiments, the kit can comprise (i) from one to eight volumes of a liquid composition (e.g., a liquid composition comprising a stimuli-responsive biocompatible polymer, a liquid composition comprising a crosslinkable biomaterial, a liquid composition comprising a non-erodible biocompatible material and a population of energy-absorbing particles, or a liquid composition comprising a heat-activated biocompatible polymer); (ii) from one to eight syringes, each syringe comprising a barrel defining a volume for containing the liquid composition, a distal end of the barrel including a delivery tip; and a plunger sized and configured to move within the volume of the barrel to convey the liquid composition through the delivery tip; (iii) from one to eight ablation probes; and (iv) from one to eight introducer cannulae, each introducer cannula comprising a central channel sized and configured to receive an ablation probe and a delivery tip therethrough.

Devices

Also provided herein are devices for guiding neural regeneration following ablation. The devices can comprise unit doses of a liquid composition described herein (e.g., a liquid composition comprising a stimuli-responsive biocompatible polymer) packaged within a syringe or other suitable implement that facilitates delivery of the liquid composition to the treatment site. The device can be sealed and sterilized so as to be ready for use by a physician while preforming a neural ablation procedure described herein.

For example, the syringe can comprise a barrel defining a volume containing from 1 mL to 10 mL (e.g., from 1 mL to 5 mL) of a liquid composition, a distal end of the barrel including a delivery tip; and a plunger sized and configured to move within the volume of the barrel to convey the liquid composition through the delivery tip. The liquid composition can comprise (i) from 20% to 40% by weight of a first inverse thermosensitive polymer defined by Formula I below

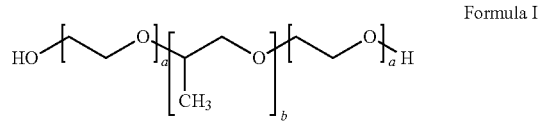

Formula I wherein a is an integer from 90 to 110 and b is an integer from 50 to 60, wherein the first inverse thermosensitive polymer has a molecular weight of from 9,500 Da to 15,000 Da, and wherein the first inverse thermosensitive polymer has a polyoxyethylene content of from 70% to 75%; and (ii) from 5% to 50% by weight of a second inverse thermosensitive polymer defined by Formula I below

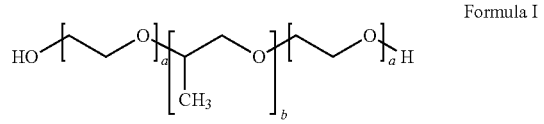

Formula I wherein a is an integer from 70 to 90 and b is an integer from 20 to 35, wherein the first inverse thermosensitive polymer has a molecular weight of from 7,500 Da to 10,000 Da, and wherein the first inverse thermosensitive polymer has a polyoxyethylene content of from 78% to 85%. The first inverse thermosensitive polymer and the second inverse thermosensitive polymer, in combination, can exhibit a transition temperature of from 10° C. to 37° C. The first inverse thermosensitive polymer and the second inverse thermosensitive polymer, in combination, can exhibit a viscosity of at least 25,000 at 37° C., such as a viscosity of from 25,000 to 100,000 cP at 37° C.

The liquid composition can be formulated so as to exhibit a viscosity of less than 1000 cP at 4° C. (e.g., to facilitate injectability).

In some embodiments, the liquid composition can further comprise a solvent (e.g., water, saline, a buffer solution, DMSO, ethanol, methanol, glutaraldehyde, or combinations thereof).

In some embodiments, the liquid composition can further comprise an active agent. The active agent can be a therapeutic agent, a prophylactic agent, a diagnostic agent, or a combination thereof. For example, the active agent can comprise an anti-nerve growth factor, an anti-inflammatory agent, an analgesic, a contrast agent, a biomarker for monitoring clearance of the polymeric matrix, an NGF/TrkA pathway inhibitor, or a combination thereof.

By way of non-limiting illustration, examples of certain embodiments of the present disclosure are given below.

EXAMPLES

Example 1: Evaluation of Stimuli-Responsive Materials

Four example stimuli-responsive (thermoresponsive) polymer compositions (TA 1, TA 2, TA 3, and TA 4) were prepared by mixing varied % by mass poloxamer solutions in cold water. Once the polymer had dissolved, a second poloxamer was added to bring the total mass of the composition to 100 g. The mixture was extremely viscous and an overhead stirring was used to aid in dissolution. The system was kept on ice to prevent an increase in viscosity. Once a homogenous solution had been achieved the system was stored in a sealed container at 4° C. The components of the four example thermoresponsive polymer compositions are included in the table below.

| Formula | Poloxamer 407 | Poloxamer 188 | Water | Additive | Comment |
| --- | --- | --- | --- | --- | --- |
| TA 1 | 20% | 5% | 75% | N/A | Watery |
| TA 2 | 20% | 15% | 65% | N/A | Semi-solid |
| TA 3 | 20% | 15% | 65% | 1% Alginate | Sticky |
| TA 4 | 30% | 0% | 70% | N/A | Thick |

Figure 3:
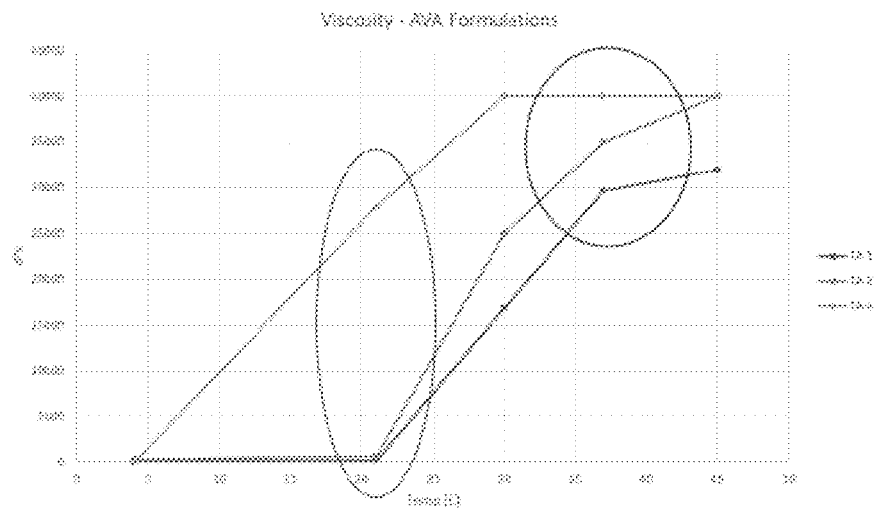
FIG. 3 is a plot showing the showing the viscosity of three different example inverse thermosensitive polymers at different temperatures (4° C., 22° C., 30° C., 37° C., 45° C.).

Viscosity—Each thermoresponsive formulation was investigated for viscosity at several temperatures (4° C., 22° C., 30° C., 37° C., and 45° C.). The viscosity was recorded using a spindle-based viscometer. It was observed that at depressed temperatures the viscosity of the solutions is low, but based on the polymer composition a significant increase in viscosity by continuously elevating the temperature. A plateauing effect was observed at temperatures above 45° C., which was attributed to the limit of detection of the instrument. The results are shown in FIG. 3.

Spread—Polyacrylamide hydrogels were prepared into 2×2×1-inch shapes. The hydrogels were then incubated at 37° C. to achieve a temperature equilibrium. In a temperature-controlled environment, the hydrogels were declined. A 500 μL sample of each thermoresponsive material (stored at room temperature or 4° C.) was added to pre-marked position on the declined hydrogel slab. The center of the addition site was marked. The system was then allowed to remain at 37° C. for a prescribed period of time. After time had expired, the endpoint of where the material had traveled was recorded and calculated as an index.

Figure 4:
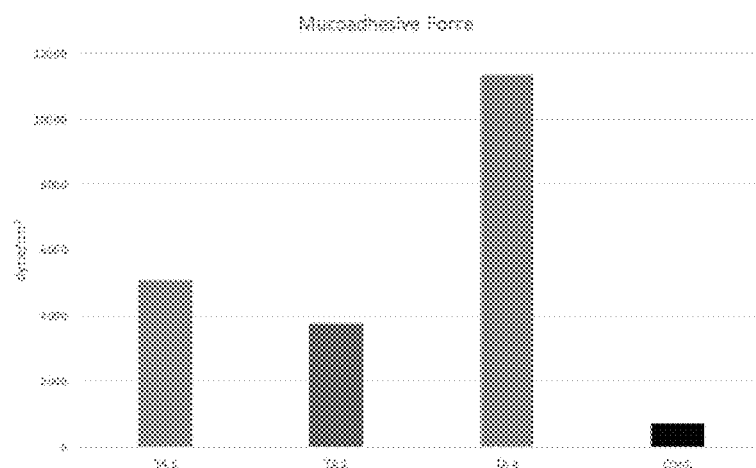
FIG. 4 is a plot showing the mucoadhesive force of three different inverse thermosensitive polymer formulations.

Mucoadhesion—To verify the adhesive properties of the polymer formulations, an adhesion test was modified from previously reported methods. In a controlled environment of 37° C., a 300 μL portion of the test article previously equilibrated to room temperature or 4° C. was placed between two polyacrylamide hydrogels with the dimensions of 2×2×1-inches. One of polyacrylamide portions was secured to a base, while the remaining piece was fixated to a hanging balance. The base was adjusted so the balance was balanced. The system was equilibrated over 5 minutes. To the opposing side of the hanging balance, a pre-weighed container was slowly filled with water. When the two portions of material would separate, the container filled with water was massed. The mass of the liquid was used to calculate the mucoadhesion provided by the formulation. The results are plotted in FIG. 4.

These thermoresponsive polymer formulations can exist as a liquid below body temp, but then solidifies near or at body temperature. The time for gelation is in a matter of seconds with minimal movement of the solidify gel from the target site. The gel will also coat, seal, plug, penetrate in any gaps in tissue and cell membranes, providing a physical barrier that can prevent of release of molecules from cells and/or signal molecules.

The effectiveness of the thermoresponsive materials in prolonging pain relief following a neural ablation procedure was evaluated in vivo using animal studies. All studies were performed on male Lewis rats (250-300 g). For the surgical procedure, a small incision was made on the thigh, adjacent to the sciatic notch. Using blunt forceps, the sciatic nerve was exposed by carefully separating surrounding connective tissue and muscle. Following this, a Coolief introducer (75 mm-long, 4 mm active tip—CRI-17-75-4, Avanos Medical) was positioned directly under the sciatic nerve. The introducer needle was then removed and the probe (CRP-17-75, CRF—Avanos Medical) was placed directly under the sciatic nerve. A bolus of saline was added directly over the exposed sciatic nerve and tissue. The impedance measurement was then taken, and if the values fell below 250 ohms, the RF generator (PMG-Advanced, Avanos) was started to deliver the electrical current.

In all animals, the RF procedure parameters were optimized for animal survival. The cooled RF ablation procedure was an RF current at 60° C. was delivered for 80 s. At the end of the procedure, the probe was removed, but the introducer was kept in place and secured with surgical tape. The animal tissue was allowed to rest and rise to body temperature. The liquid composition comprising the thermoresponsive material was then secured to the introducer and 300 µL of the liquid composition was injected through the introducer. After injection, the introducer was removed and the animal was allowed to recover.

Figure 5:
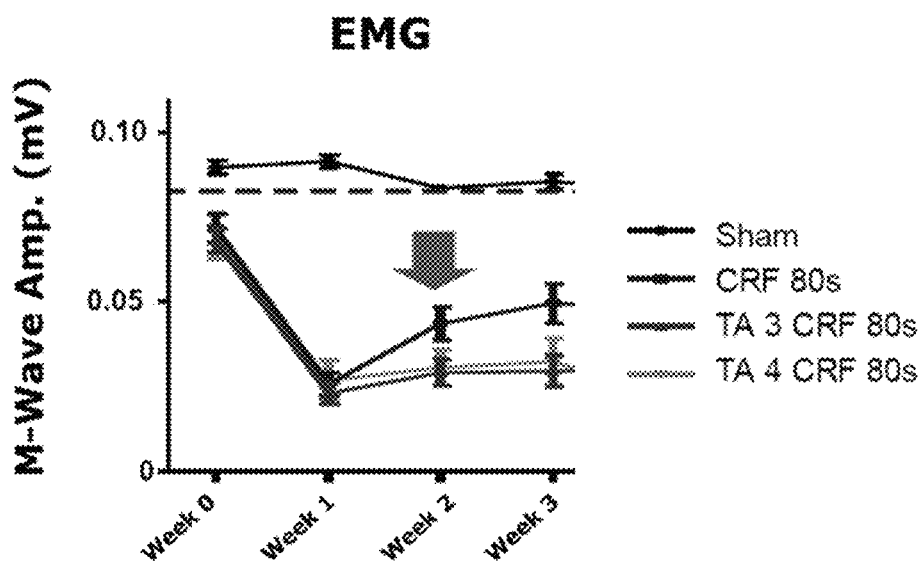
FIG. 5 is a plot showing the muscle contraction response by electromyography as represented by percentage recovery from baseline.

Animals were sedated, and electrodes were placed on the lower leg extremity. Muscle contraction in response to electrical stimulation was measured to evaluate nerve function following ablation. FIG. 5 is a plot showing the muscle contraction response by electromyography as represented by percentage recovery from baseline. The plot includes data for animals immediately post treatment, 7 days after treatment, 14 days after treatment, and 21 days after treatment with ablation alone (CRF 80s), ablation along with TA-3 (CRF 80s TA 3), and ablation along with TA 4 (CRF 80s TA 4). A control (no ablation or injection of stimuli-responsive polymer (Sham)) is included for reference. As shown in FIG. 5, animals treated with stimuli-responsive polymer in addition to ablation showed a more prolonged depression in motor activity over three weeks as compared to animals treated with ablation alone. This suggests that the polymeric matrix formed at the lesion site modulates neural response.

Animals were sacrificed, and sciatic nerves were excised, either immediately following the ablation (T=0 h), seven days, or fourteen days following the ablation. All nerves were immediately fixed in 10% neutral buffered formalin after isolation and shipped to a third-party lab for processing and analysis.

Formalin-fixed rat nerve samples were submitted and processed intact. Nerves were bisected following processing and were embedded to create proximal cross sections. Nerves were embedded such that the superficial block contained the central portion of the nerve; deep in the block, the ends of the nerve sample were present. Blocks were sectioned with 300 µm between slides (4 µm thick sections) to span the lesioned area (between 11 and 23 slides per nerve).

A single nerve had 40 slides taken, spaced 150 µm apart. All slides were stained with hematoxylin and eosin (H&E). For each nerve, five levels spaced through the ablation and/or cooled zones were selected for pathologic evaluation. Glass slides were evaluated by a board-certified veterinary pathologist using light microscopy. Histologic lesion extent and/or severity was scored 0-5, where 0=absent, 1=minimal, 2=mild, 3=moderate, 4=marked, 5=severe.

Figure 6:
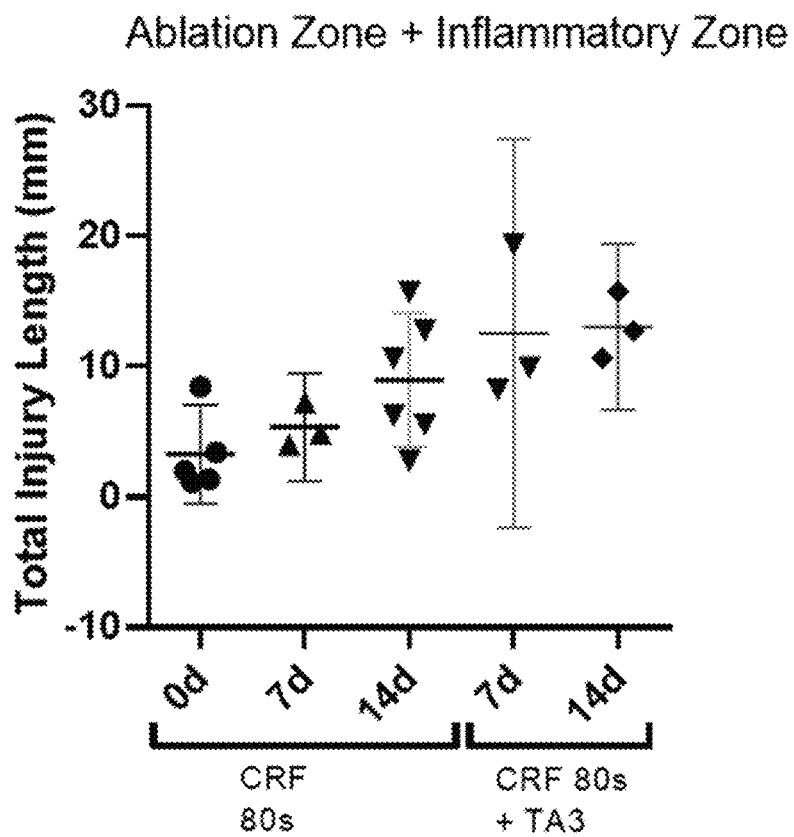
FIG. 6 is a plot showing the quantification of ablation length of CRF lesions and CRF lesions with the addition of the polymeric barrier (TA3) for Day 7 and 14.

FIG. 6 is a plot showing the ablation length of CRF lesions with and without treatment with stimuli-responsive composition TA 3 at Day 7 and Day 14 following ablation.

Figure 7A:
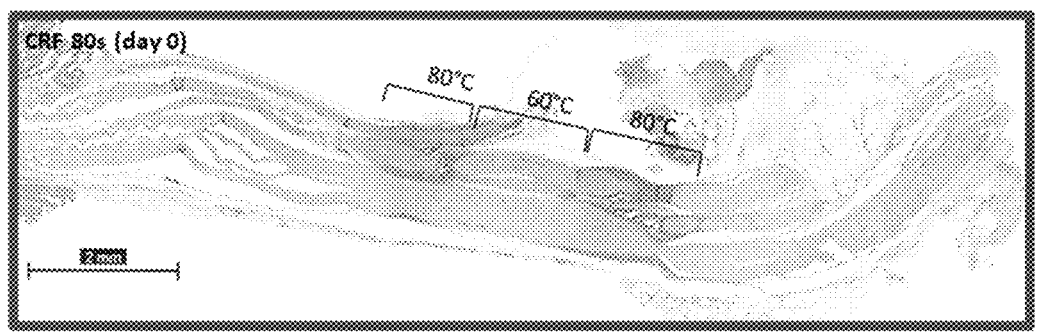
FIGS. 7A-7D show the results of histology studies.
Figure 7B:
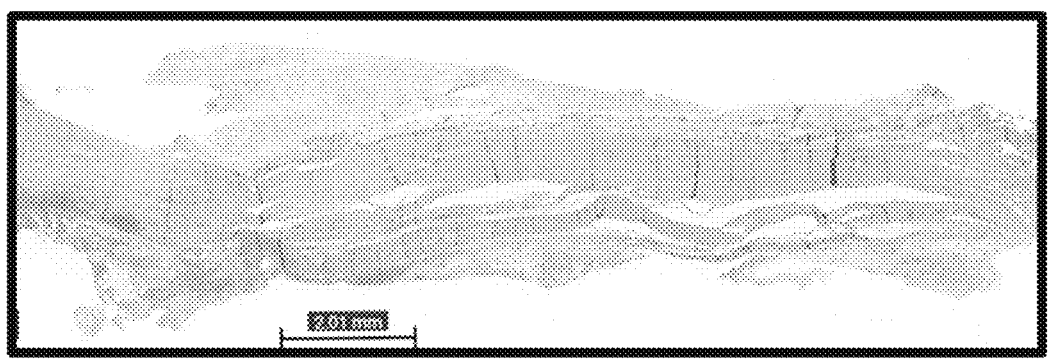
Figure 7C:
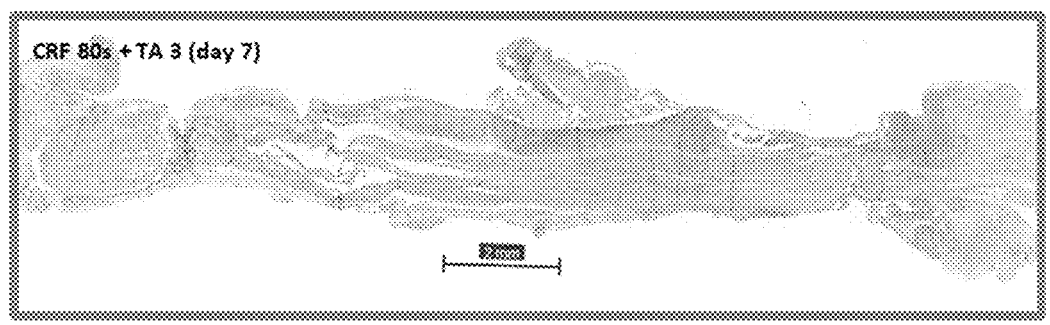
Figure 7D:
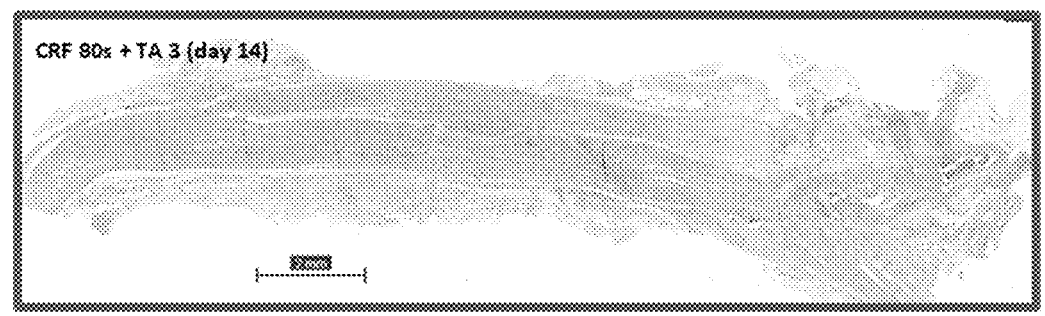

FIGS. 7A-7D show histology images of sciatic nerve tissue ablations. FIGS. 7A and 7B show an image of CRF treated nerve following ablation (Day 0, FIG. 7A; and Day 7 following treatment, FIG. 7B). FIGS. 7C and 7D show an image of CRF treated nerve following ablation and treatment with thermoresponsive composition TA 3 (Day 7 following treatment, FIG. 7C; and Day 14 following treatment, FIG. 7D).

When neural ablation is preformed, the surgical site returns to physiological temperature shortly following ablation. Subsequently, a liquid composition comprising a thermoresponsive polymer composition is introduced through the ablation equipment (e.g., the introducer) to the target site. The ablation equipment is then removed and the surgical site is sealed. The animal is then allowed to recover. These preliminary results indicate that addition of the thermoresponsive polymer extends the duration of the efficacy of the ablation procedure.

Example 2. Evaluation of Crosslinkable Biomaterial

An ablation procedure was performed on the sciatic nerve of a rat. Briefly, a small incision was made on the thigh, adjacent to the sciatic notch. Using blunt forceps, the sciatic nerve was exposed by carefully separating surrounding connective tissue and muscle. Following this, a Coolief introducer (75 mm-long, 4 mm active tip—CRI-17-75-4, Avanos Medical) was positioned directly under the sciatic nerve. The introducer needle was then removed and the probe (CRP-17-75, CRF—Avanos Medical) was placed directly under the sciatic nerve. A bolus of saline was added directly over the exposed sciatic nerve and tissue. The impedance measurement was then taken, and if the values fell below 250 ohms, the RF generator (PMG-Advanced, Avanos) was started to deliver the electrical current. In all animals, the RF procedure parameters were optimized for animal survival. The cooled RF ablation procedure was an RF current at 60° C. was delivered for 80 s. At the end of the procedure, the probe and introducer were removed.

Figure 8:
FIG. 8 is a photograph showing the application of a crosslinkable biomaterial to an ablation site.
Figure 9:
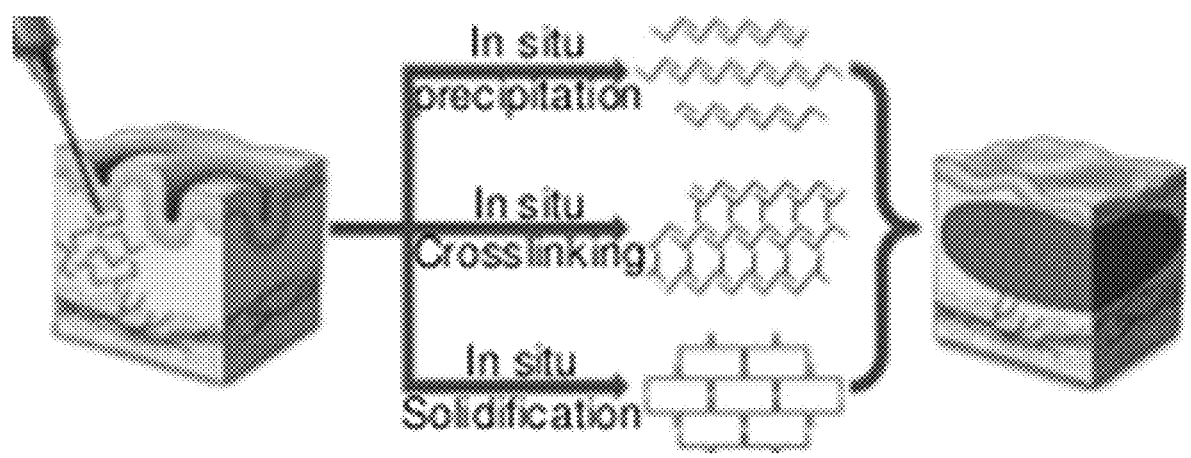
FIG. 9 is a schematic illustration showing pathways for the formation of semi-solid (gel) and liquid matrices from a liquid composition in the human body.

100 microliters of each DuraSeal composition was injected into the injury site. The incision was closed and the animal was kept warm for 15 minutes. After 15 minutes, the wound was re-opened, and the lesion site was visually inspected to confirm formation of the polymeric matrix. FIG. 8 includes a photograph of the polymeric matrix formed at the lesion site. As shown in FIG. 8, within 15 minutes, the crosslinkable biomaterial had reacted at the lesion side, and formed a matrix enclosing the lesion without visible migration.

The compositions, devices, kits, systems, and methods of the appended claims are not limited in scope by the specific compositions, devices, kits, systems, and methods described herein, which are intended as illustrations of a few aspects of the claims. Any compositions, devices, kits, systems, and methods that are functionally equivalent are intended to fall within the scope of the claims. Various modifications of the compositions, devices, kits, systems, and methods in addition to those shown and described herein are intended to fall within the scope of the appended claims. Further, while only certain representative compositions, components, devices, kits, systems, and method steps disclosed herein are specifically described, other combinations of the compositions, devices, kits, systems, and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than where noted, all numbers expressing geometries, dimensions, and so forth used in the specification and claims are to be understood at the very least, and not as an attempt to limit the application of the doctrine of equivalents to the scope of the claims, to be construed in light of the number of significant digits and ordinary rounding approaches.

Unless defined otherwise, all technical and scientific terms used herein have the same meanings as commonly understood by one of skill in the art to which the disclosed invention belongs. Publications cited herein and the materials for which they are cited are specifically incorporated by reference.

What is claimed is:

1. A method for ameliorating pain in a subject in need thereof, the method comprising:
    inserting an introducer cannula into the subject and positioning a distal end of the introducer cannula proximate a treatment site comprising a nerve that transmits a pain impulse;
    injecting a liquid composition comprising a heat-activated biocompatible polymer through the introducer cannula and into the treatment site,
    advancing an ablation probe through the introducer to a region proximate to the treatment site;
    ablating the nerve with the ablation probe, thereby forming a lesion on the nerve; retracting the ablation probe;
    wherein the liquid composition exhibits a viscosity of less than 1000 cP at 4° C.;
    wherein upon heating to a temperature of from 40° C. to 70° C., the heat-activated biocompatible polymer forms a polymeric matrix that exhibits a viscosity of at least 25,000 cP at 37° C.; and
    wherein the heat generated by the ablation probe induces the heat-activated biocompatible polymer to form the polymeric matrix at the treatment site.

2. The method of claim 1, wherein the ablation probe comprises radiofrequency (RF) ablation probe, and the ablating step comprises applying energy using the RF probe to ablate the nerve.

3. The method of claim 1, wherein the introducer cannula is actively or passively cooled during the ablating step, during the injecting step, or any combination thereof.

4. The method of claim 1, wherein the polymeric matrix is a solid or gel.

5. The method of claim 1, wherein the polymeric matrix substantially surrounds the lesion.

6. The method of claim 1, wherein at least a portion of the polymeric matrix remains at the treatment site at least 72 hours after injection.

7. The method of claim 1, wherein the polymeric matrix further comprises a contrast agent, and wherein the method further comprises imaging the matrix to confirm placement of the matrix at the treatment site, to monitor clearance of the matrix from the treatment site, or any combination thereof.

8. The method of claim 1, wherein the heat-activated biocompatible polymer comprises a crosslinkable polymer and a thermally activated crosslinker.

9. The method of claim 8, wherein the thermally activated crosslinker comprises a crosslinking agent encapsulated in a lipid vesicle.

10. The method of claim 8, wherein the crosslinkable polymer comprises a polymer selected from the group consisting of polylactides, polyglycolides, polycaprolactones, polyanhydrides, polyamines, polyurethanes, polyesteramides, poly(alkylene oxides), polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polydimethylsiloxanes, polyhydroxycellulose, chitin, alginates, chitosan, hyaluronic acid, and copolymers, terpolymers and mixtures thereof.

11. The method of claim 8, wherein the crosslinkable polymer is crosslinked by the thermally activated crosslinker at a temperature of from 40° C. to 70° C.

12. A system for neural ablation comprising:
    (i) a liquid composition comprising a heat-activated biocompatible polymer;
    (ii) a syringe comprising
        a barrel defining a volume for containing the liquid composition, a distal end of the barrel including a delivery tip; and
        a plunger sized and configured to move within the volume of the barrel to convey the liquid composition through the delivery tip;
    (iii) an ablation probe; and
    (iv) an introducer cannula comprising a central channel sized and configured to receive the ablation probe and the delivery tip therethrough;
    wherein the liquid composition exhibits a viscosity of less than 1000 cP at 4° C.; and
    wherein upon heating to a temperature of from 40° C. to 70° C., the heat-activated biocompatible polymer forms a polymeric matrix that exhibits a viscosity of at least 25,000 cP at 37° C.

13. The system of claim 12, wherein the ablation probe is an actively or passively cooled ablation probe.

14. The system of claim 12, wherein the liquid composition is loaded in the barrel of the syringe.

15. The system of claim 12, wherein the heat-activated biocompatible polymer comprises a crosslinkable polymer and a thermally activated crosslinker.

16. The system of claim 15, wherein the thermally activated crosslinker comprises a crosslinking agent encapsulated in a lipid vesicle.

17. The system of claim 15, wherein the crosslinkable polymer comprises a polymer selected from the group consisting of polylactides, polyglycolides, polycaprolactones, polyanhydrides, polyamines, polyurethanes, polyesteramides, poly(alkylene oxides), polyorthoesters, polydioxanones, polyacetals, polyketals, polycarbonates, polyphosphoesters, polyoxaesters, polyorthocarbonates, polyphosphazenes, succinates, poly(malic acid), poly(amino acids), polyvinylpyrrolidone, polyethylene glycol, polydimethylsiloxanes, polyhydroxycellulose, chitin, alginates, chitosan, hyaluronic acid, and copolymers, terpolymers and mixtures thereof.

18. The system of claim 15, wherein the crosslinkable polymer is crosslinked by the thermally activated crosslinker at a temperature of from 40° C. to 70° C.

19. A kit for performing a neural ablation procedure comprising the system of claim 12 enclosed within sterile packaging.

* * * * *